(12) United States Patent  (10) Patent No.: US 8,759,361 B2
Bakthavatchalam et al.  (45) Date of Patent: Jun. 24, 2014

(54) 2-PHENOXY PYRIMIDINONE ANALOGUES

(75) Inventors: Rajagopal Bakthavatchalam, Madison, CT (US); Scott M. Capitosti, Middletown, CT (US); Jianjun Xu, Branford, CT (US); Bertrand L. Chenard, Waterford, CT (US); Manuka Ghosh, Madison, CT (US); Charles A. Blum, Westbrook, CT (US)

(73) Assignee: Neurogen Corporation, Branford, CT (US)

( * ) Notice: Subject to any disclaimer, the term of this patent is extended or adjusted under 35 U.S.C. 154(b) by 54 days.

(21) Appl. No.: 13/215,195

(22) Filed: Aug. 22, 2011

(65) Prior Publication Data

US 2012/0208829 A1  Aug. 16, 2012

Related U.S. Application Data

(63) Continuation of application No. 11/895,286, filed on Aug. 22, 2007, now Pat. No. 8,003,656.

(60) Provisional application No. 60/823,258, filed on Aug. 23, 2006.

(51) Int. Cl.
A61K 31/522 (2006.01)
A61P 25/04 (2006.01)
A61P 17/04 (2006.01)
A61P 13/10 (2006.01)
C07D 473/04 (2006.01)
C07D 495/04 (2006.01)
C07D 487/04 (2006.01)
A61K 31/519 (2006.01)

(52) U.S. Cl.
USPC ............. 514/263.22; 514/263.34; 514/263.3; 514/260.1; 514/264.1; 544/269; 544/267; 544/278; 544/262; 544/279

(58) Field of Classification Search
USPC ........................................ 514/263.22, 263.34
See application file for complete search history.

(56) References Cited

U.S. PATENT DOCUMENTS

| | | | |
|---|---|---|---|
| 5,124,331 | A | 6/1992 | Arita et al. |
| 5,202,328 | A | 4/1993 | de Laszlo et al. |
| 5,962,457 | A | 10/1999 | Chenard et al. |
| 6,136,812 | A | 10/2000 | Chenard et al. |
| 6,323,208 | B1 | 11/2001 | Chenard et al. |
| 6,921,764 | B2 | 7/2005 | Chenard et al. |
| 8,003,656 | B2 | 8/2011 | Bakthavatchalam et al. |
| 2003/0004172 | A1 | 1/2003 | Harter et al. |
| 2003/0236280 | A1 | 12/2003 | Codd et al. |
| 2004/0132732 | A1 | 7/2004 | Han et al. |
| 2004/0242566 | A1 | 12/2004 | Feng et al. |
| 2005/0165049 | A1 | 7/2005 | Hulme et al. |
| 2007/0135454 | A1 | 6/2007 | Bayliss et al. |
| 2008/0090845 | A1 | 4/2008 | Blum et al. |
| 2010/0008866 | A1 | 1/2010 | Blum et al. |

FOREIGN PATENT DOCUMENTS

| | | |
|---|---|---|
| WO | WO-98/49899 | 11/1998 |
| WO | WO-02/26718 | 4/2002 |
| WO | WO-02/076946 A2 | 10/2002 |
| WO | WO-03/055848 | 7/2003 |
| WO | WO-03/106435 A1 | 12/2003 |
| WO | WO-2004/028440 | 4/2004 |
| WO | WO-2004/033435 A1 | 4/2004 |
| WO | WO-2004/037176 A2 | 5/2004 |
| WO | WO-2005/049601 A1 | 6/2005 |
| WO | WO-2005/049613 A1 | 6/2005 |
| WO | WO-2005/120510 A1 | 12/2005 |
| WO | WO-2006/047516 A2 | 5/2006 |
| WO | WO-2006/120481 A2 | 11/2006 |
| WO | WO2006/122200 A1 | 11/2006 |
| WO | WO-2007/056124 A2 | 5/2007 |
| WO | WO-2008/156607 | 12/2008 |
| WO | WO-2009/100403 | 8/2009 |
| WO | WO-2009/121036 | 10/2009 |

OTHER PUBLICATIONS

Anquetin, G. et al., "Synthesis of New Fluoroquinolones and Evaluation of their In Vitro Activity on *Toxoplasma gondii* and *Plasmodium* spp.," Bioorganic & Medicinal Chemistry Letters, vol. 14, pp. 2773-2776, (2004).

Sako, Magoichi et al., "New and Facile Synthesis of 5,6,7,8-Tetrahydro-5-deaza-5-thiapterins via the Aliphatic S-N Type Smiles Rearrangement," Chem. Pharm. Bull., vol. 42(4), pp. 806-810, (1994).

Rokosz, Laura, "Discovery and Development of Melanin-Concentrating Hormone Receptor 1 antagonists for the Treatment of Obesity," Expert Opin. Drug Discov., vol. 2(10), pp. 1301-1327, (2007).

(Continued)

*Primary Examiner* — Susanna Moore
(74) *Attorney, Agent, or Firm* — Edwards Wildman Palmer LLP; Pater F. Corless; Mark D. Russett

(57) ABSTRACT

2-Phenoxy pyrimidinone analogues are provided, of the Formula:

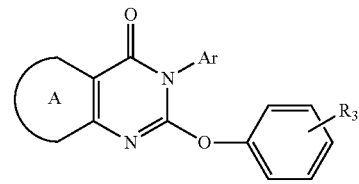

wherein variables are as described herein. Such compounds are ligands that may be used to modulate specific receptor activity in vivo or in vitro, and are particularly useful in the treatment of conditions associated with pathological receptor activation in humans, domesticated companion animals and livestock animals. Pharmaceutical compositions and methods for using such compounds to treat such disorders are provided, as are methods for using such ligands for receptor localization studies.

14 Claims, No Drawings

(56) References Cited

OTHER PUBLICATIONS

International Search Report and Written Opinion dated Sep. 8, 2008, from corresponding PCT Application No. PCT/US07/18654.
Opposition filed in the name of Asociacion de la Industria Farmacéutica Nacional Asifan dated Jul. 21, 2009, in corresponding Costa Rica Patent Application No. 10675 (English translation).
McNaught et al., "cycloalkyl groups", IUPAC Ed, [Online] Jan. 1, 1997, Compendium of Chemical Terminology: Iupac Recommendations; [IUPAC Chemical Data Series], Blackwell Science, Oxford [U.A.], XP002585006, ISBN: 978-0-86542-684-9 Retrieved from the Internet: URL:http://www.iupac.org/goldbook/C01498.pdf>.
McNaught et al., "alkyl groups", IUPAC Ed, [Online], Jan. 1, 1997, Compendium of Chemical Terminology: Iupac Recommendations; [IUPAC Chemical Data Series], Blackwell Science, Oxford [U.A.], XP002585005, ISBN: 978-0-86542-684-9, Retrieved from the Internet: URL:http://www.iupac.org/goldbook/A00228.pdf>.
Supplementary European Search Report and Opinion dated Aug. 10, 2010, in corresponding European Application No. 07811503.7.
Johansen, M. E., et al., "TRPV1 Antagonists Elevate Cell Surface Populations of Receptor Protein and Exacerbate TRPV1-Mediated Toxicities in Human Lung Epithelial Cells," Toxicological Sciences, 89(1), 278-286 (2006) (Advance Access publication Aug. 24, 2005).
Thomas, Karen C. et al., "Transient Receptor Potential Vanilloid 1 Agonists Cause Endoplasmic Reticulum Stress and Cell Death in Human Lung Cells", The Journal of Pharmacology and Experimental Therapeutics, vol. 321, pp. 830-838, (2007).
Bolcskei, Kata et al.,"Investigation of the role of TRPV1 receptors in acute and chronic nociceptive processes using gene-deficient mice," Pain 117, pp. 368-376, (2005).
Helyes, Zsuzsanna et al., "Role of transient receptor potential vanilloid 1 receptors in endotoxin-induced airway inflammation in the mouse," Am J Physiol Lung Cell Mol Physiol., vol. 292, pp. L1173-L1181, (2007).
Banvolgyi, Agnes et al., "Evidence for a novel protective role of the vanilloid TRPV1 receptor in a cutaneous contact allergic dermatitis model," J. Neuroimmunology, vol. 169, pp. 86-96, (2005).
Xiang et al., "Effects of airway inflammation on cough response in the guinea pig", J. Applied Physiol., 85:1847-54 (1998).
Trevisani et al., "Antitussive activity of iodo-resiniferatoxin in guinea pigs", Thorax 59:769-772 (2004).
Sasaki et al., "Effect of NS-21, an Anticholinergic Drug with Calcium Antagonistic Activity, on Lower Urinary Tract Function in a Rat Model of Urinary Frequency", Int. J. Urol., 4:401-406 (1997).
Szallasi et al., "Vanilloid Receptor TRPV1 Antagonists as the Next Generation of Painkillers. Are We Putting the Cart before the Horse?", J. Med Chem. 47(11):2717-2723 (2004).

2-PHENOXY PYRIMIDINONE ANALOGUES

CROSS-REFERENCE TO RELATED APPLICATIONS

This application is a continuation of U.S. patent application Ser. No. 11/895,286, filed Aug. 22, 2007, now U.S. Pat. No. 8,003,656, issued Aug. 23, 2011, which claims priority to U.S. Provisional Application 60/823,258, filed Aug. 23, 2006. The contents of each of the foregoing applications are hereby incorporated by reference in their entirety.

FIELD OF THE INVENTION

This invention relates generally to 2-phenoxy pyrimidinone analogues that have useful pharmacological properties. The invention further relates to the use of such compounds for treating conditions related to capsaicin receptor activation, for identifying other agents that bind to capsaicin receptor, and as probes for the detection and localization of capsaicin receptors.

BACKGROUND OF THE INVENTION

Pain perception, or nociception, is mediated by the peripheral terminals of a group of specialized sensory neurons, termed "nociceptors." A wide variety of physical and chemical stimuli induce activation of such neurons in mammals, leading to recognition of a potentially harmful stimulus. Inappropriate or excessive activation of nociceptors, however, can result in debilitating acute or chronic pain.

Neuropathic pain involves pain signal transmission in the absence of stimulus, and typically results from damage to the nervous system. In most instances, such pain is thought to occur because of sensitization in the peripheral and central nervous systems following initial damage to the peripheral system (e.g., via direct injury or systemic disease). Neuropathic pain is typically burning, shooting and unrelenting in its intensity and can sometimes be more debilitating that the initial injury or disease process that induced it.

Existing treatments for neuropathic pain are largely ineffective. Opiates, such as morphine, are potent analgesics, but their usefulness is limited because of adverse side effects, such as physical addictiveness and withdrawal properties, as well as respiratory depression, mood changes, and decreased intestinal motility with concomitant constipation, nausea, vomiting, and alterations in the endocrine and autonomic nervous systems. In addition, neuropathic pain is frequently non-responsive or only partially responsive to conventional opioid analgesic regimens. Treatments employing the N-methyl-D-aspartate antagonist ketamine or the alpha(2)-adrenergic agonist clonidine can reduce acute or chronic pain, and permit a reduction in opioid consumption, but these agents are often poorly tolerated due to side effects.

Topical treatment with capsaicin has been used to treat chronic and acute pain, including neuropathic pain. Capsaicin is a pungent substance derived from the plants of the Solanaceae family (which includes hot chili peppers) and appears to act selectively on the small diameter afferent nerve fibers (A-delta and C fibers) that are believed to mediate pain. The response to capsaicin is characterized by persistent activation of nociceptors in peripheral tissues, followed by eventual desensitization of peripheral nociceptors to one or more stimuli. From studies in animals, capsaicin appears to trigger C fiber membrane depolarization by opening cation selective channels for calcium and sodium.

Similar responses are also evoked by structural analogues of capsaicin that share a common vanilloid moiety. One such analogue is resiniferatoxin (RTX), a natural product of *Euphorbia* plants. The term vanilloid receptor (VR) was coined to describe the neuronal membrane recognition site for capsaicin and such related irritant compounds. The capsaicin response is competitively inhibited (and thereby antagonized) by another capsaicin analog, capsazepine, and is also inhibited by the non-selective cation channel blocker ruthenium red, which binds to VR with no more than moderate affinity (typically with a $K_i$ value of no lower than 140 µM).

Rat and human vanilloid receptors have been cloned from dorsal root ganglion cells. The first type of vanilloid receptor to be identified is known as vanilloid receptor type 1 (VR1), and the terms "VR1" and "capsaicin receptor" are used interchangeably herein to refer to rat and/or human receptors of this type, as well as mammalian homologues. The role of VR1 in pain sensation has been confirmed using mice lacking this receptor, which exhibit no vanilloid-evoked pain behavior and impaired responses to heat and inflammation. VR1 is a nonselective cation channel with a threshold for opening that is lowered in response to elevated temperatures, low pH, and capsaicin receptor agonists. Opening of the capsaicin receptor channel is generally followed by the release of inflammatory peptides from neurons expressing the receptor and other nearby neurons, increasing the pain response. After initial activation by capsaicin, the capsaicin receptor undergoes a rapid desensitization via phosphorylation by cAMP-dependent protein kinase.

Because of their ability to desensitize nociceptors in peripheral tissues, VR1 agonist vanilloid compounds have been used as topical anesthetics. However, agonist application may itself cause burning pain, which limits this therapeutic use. Recently, it has been reported that VR1 antagonists, including certain nonvanilloid compounds, are also useful for the treatment of pain (see, e.g., PCT International Application Publication Numbers WO 02/08221, WO 03/062209, WO 04/054582, WO 04/055003, WO 04/055004, WO 04/056774, WO 05/007646, WO 05/007648, WO 05/007652, WO 05/009977, WO 05/009980, WO 05/009982, WO 05/049601, WO 05/049613, WO 06/122200 and WO 06/120481).

Thus, compounds that interact with VR1, but do not elicit the initial painful sensation of VR1 agonist vanilloid compounds, are desirable for the treatment of chronic and acute pain, including neuropathic pain, as well as other conditions that are responsive to capsaicin receptor modulation. The present invention fulfills this need, and provides further related advantages.

SUMMARY OF THE INVENTION

The present invention provides 2-phenoxy pyrimidinone analogues of Formula A:

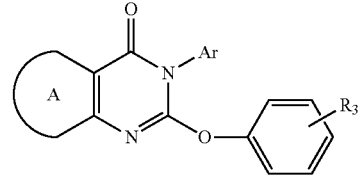

Formula A as well as pharmaceutically acceptable salts, solvates (e.g., hydrates) and esters of such compounds.

Within Formula A:

[ring structure labeled A]

represents a fused 5- or 6-membered heteroaryl that contains 1, 2 or 3 heteroatoms in the ring, said heteroatoms being independently chosen from O, N and S, with the remaining ring atoms being carbon, wherein the fused heteroaryl is optionally substituted; preferably the fused heteroaryl is substituted with from 0 to 3, or from 0 to 2, substituents independently chosen from amino, hydroxy, $C_1$-$C_6$alkyl, $C_1$-$C_6$hydroxyalkyl, ($C_3$-$C_7$cycloalkyl)$C_0$-$C_2$alkyl, $C_1$-$C_6$haloalkyl, $C_1$-$C_6$alkoxy, $C_2$-$C_6$alkyl ether, $C_1$-$C_6$alkanoyloxy, $C_1$-$C_6$alkylsulfonylamino, $C_1$-$C_6$alkanonylamino, and mono- or di-($C_1$-$C_6$alkyl)amino;

Ar is phenyl or a 5- or 6-membered heteroaryl, each of which is optionally substituted, and each of which is preferably substituted with from 0 to 4 or from 0 to 3 substituents that are independently chosen from halogen, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl)amino; and $R_3$ represents from 0 to 4, or from 0 to 3, substituents, which substituents are preferably independently chosen from halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, mono- or di-($C_1$-$C_6$alkyl) amino, and mono- or di-($C_1$-$C_6$alkyl)aminosulfonyl.

The present invention further provides 2-phenoxy pyrimidinone analogues of Formula I:

Formula I

[chemical structure]

as well as pharmaceutically acceptable salts, solvates (e.g., hydrates) and esters of such compounds.

Within Formula I:

[ring structure labeled A]

and $R_3$ are as described for Formula A;

X is N or CH that is optionally substituted with a substituent represented by $R_1$; and $R_1$ represents from 0 to 3 substituents; which substituents are preferably independently chosen from halogen, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl)amino.

Within certain aspects, compounds of Formula A and Formula I are VR1 modulators and exhibit a $K_i$ of no greater than 1 micromolar, 500 nanomolar, 100 nanomolar, 50 nanomolar, 10 nanomolar or 1 nanomolar in a capsaicin receptor binding assay and/or have an $EC_{50}$ or $IC_{50}$ value of no greater than 1 micromolar, 500 nanomolar, 100 nanomolar, 50 nanomolar, 10 nanomolar or 1 nanomolar in an in vitro assay for determination of capsaicin receptor agonist or antagonist activity. In certain embodiments, such VR1 modulators are VR1 antagonists and exhibit no detectable agonist activity in an in vitro assay of capsaicin receptor activation (e.g., the assay provided in Example 6, herein) at a concentration equal to the $IC_{50}$, 10 times the $IC_{50}$ or 100 times the $IC_{50}$.

Within certain aspects, compounds provided herein are labeled with a detectable marker (e.g., radiolabeled or fluorescein conjugated).

The present invention further provides, within other aspects, pharmaceutical compositions comprising at least one 2-phenoxy pyrimidinone analogue in combination with a physiologically acceptable carrier or excipient.

Within further aspects, methods are provided for reducing calcium conductance of a cellular capsaicin receptor, comprising contacting a cell (e.g., neuronal, such as cells of the central nervous system or peripheral ganglia, urothelial or lung) that expresses a capsaicin receptor with at least one VR1 modulator as described herein. Such contact may occur in vivo or in vitro and is generally performed using a concentration of VR1 modulator that is sufficient to alter the binding of vanilloid ligand to VR1 in vitro (using the assay provided in Example 5) and/or VR1-mediated signal transduction (using an assay provided in Example 6).

Methods are further provided for inhibiting binding of vanilloid ligand to a capsaicin receptor. Within certain embodiments, the inhibition takes place in vitro. Such methods comprise contacting a capsaicin receptor with at least one VR1 modulator as described herein, under conditions and in an amount or concentration sufficient to detectably inhibit vanilloid ligand binding to the capsaicin receptor. Within other embodiments, the capsaicin receptor is in a patient. Such methods comprise contacting cells expressing a capsaicin receptor in a patient with at least one VR1 modulator as described herein in an amount or concentration that would be sufficient to detectably inhibit vanilloid ligand binding to cells expressing a cloned capsaicin receptor in vitro.

The present invention further provides methods for treating a condition responsive to capsaicin receptor modulation in a patient, comprising administering to the patient a therapeutically effective amount of at least one VR1 modulator as described herein.

Within other aspects, methods are provided for treating pain in a patient, comprising administering to a patient suffering from (or at risk for) pain a therapeutically effective amount of at least one VR1 modulator as described herein.

Methods are further provided for treating itch, urinary incontinence, overactive bladder, menopause symptoms, cough and/or hiccup in a patient, comprising administering to a patient suffering from (or at risk for) one or more of the foregoing conditions a therapeutically effective amount of at least one VR1 modulator as described herein.

Within other aspects, methods are provided for treating menopause symptoms in a patient, comprising administering to a patient suffering from (or at risk for) such symptoms a therapeutically effective amount of at least one VR1 modulator as described herein.

The present invention further provides methods for promoting weight loss in an obese patient, comprising administering to an obese patient a therapeutically effective amount of at least one VR1 modulator as described herein.

Methods are further provided for identifying an agent that binds to capsaicin receptor, comprising: (a) contacting capsaicin receptor with a labeled compound as described herein under conditions that permit binding of the compound to capsaicin receptor, thereby generating bound, labeled compound; (b) detecting a signal that corresponds to the amount of bound, labeled compound in the absence of test agent; (c) contacting the bound, labeled compound with a test agent; (d) detecting a signal that corresponds to the amount of bound labeled compound in the presence of test agent; and (e) detecting a decrease in signal detected in step (d), as compared to the signal detected in step (b).

Within further aspects, the present invention provides methods for determining the presence or absence of capsaicin receptor in a sample, comprising: (a) contacting a sample with a compound as described herein under conditions that permit binding of the compound to capsaicin receptor; and (b) detecting a signal indicative of a level of the compound bound to capsaicin receptor.

The present invention also provides packaged pharmaceutical preparations, comprising: (a) a pharmaceutical composition as described herein in a container; and (b) instructions for using the composition to treat one or more conditions responsive to capsaicin receptor modulation, such as pain, itch, urinary incontinence, overactive bladder, menopause symptoms, cough, hiccup and/or obesity.

In yet another aspect, the present invention provides methods for preparing the compounds disclosed herein, including the intermediates.

These and other aspects of the invention will become apparent upon reference to the following detailed description.

DETAILED DESCRIPTION

As noted above, the present invention provides 2-phenoxy pyrimidinone analogues. Such compounds may be used in vitro or in vivo, to modulate capsaicin receptor activity in a variety of contexts.

Terminology

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that includes variables (e.g., $R_1$, A). Unless otherwise specified, each variable within such a formula is defined independently of any other variable, and any variable that occurs more than one time in a formula is defined independently at each occurrence.

The phrase "2-phenoxy pyrimidinone analogues," as used herein, encompasses all compounds of Formula A, including those of Formula I, as well as compounds of other Formulas provided herein (including any enantiomers, racemates and stereoisomers) and pharmaceutically acceptable salts, solvates and esters of such compounds.

A "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutically acceptable anions for use in salt formation include, but are not limited to, acetate, 2-acetoxybenzoate, ascorbate, benzoate, bicarbonate, bromide, calcium edetate, carbonate, chloride, citrate, dihydrochloride, diphosphate, ditartrate, edetate, estolate (ethylsuccinate), formate, fumarate, gluceptate, gluconate, glutamate, glycolate, glycollylarsanilate, hexylresorcinate, hydrabamine, hydrobromide, hydrochloride, hydroiodide, hydroxymaleate, hydroxynaphthoate, iodide, isethionate, lactate, lactobionate, malate, maleate, mandelate, methylbromide, methylnitrate, methylsulfate, mucate, napsylate, nitrate, pamoate, pantothenate, phenylacetate, phosphate, polygalacturonate, propionate, salicylate, stearate, subacetate, succinate, sulfamate, sulfanilate, sulfate, sulfonates including besylate (benzenesulfonate), camsylate (camphorsulfonate), edisylate (ethane-1,2-disulfonate), esylate (ethanesulfonate), 2-hydroxyethylsulfonate, mesylate (methanesulfonate), triflate (trifluoromethanesulfonate) and tosylate (p-toluenesulfonate), tannate, tartrate, teoclate and triethiodide. Similarly, pharmaceutically acceptable cations for use in salt formation include, but are not limited to ammonium, benzathine, chloroprocaine, choline, diethanolamine, ethylenediamine, meglumine, procaine, and metals such as aluminum, calcium, lithium, magnesium, potassium, sodium and zinc. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, methanol, isopropanol or acetonitrile, is preferred.

It will be apparent that each compound provided herein may, but need not, be formulated as a solvate (e.g., hydrate) or non-covalent complex. In addition, the various crystal forms and polymorphs are within the scope of the present invention. Also provided herein are prodrugs of the compounds of the recited Formulas. A "prodrug" is a compound that may not fully satisfy the structural requirements of the compounds provided herein, but is modified in vivo, following administration to a patient, to produce a compound a formula provided herein. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxy, amino, or sulfhydryl group, respectively. Examples of prodrugs include, but are not limited to, acetate, formate and benzoate derivatives of alcohol and amine functional groups within the compounds provided herein. Prodrugs of the compounds provided herein may be prepared by modifying functional groups present in the compounds in such a way that the modifications are cleaved in vivo to yield the parent compounds.

As used herein, the term "alkyl" refers to a straight or branched chain saturated aliphatic hydrocarbon. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. "$C_0$-$C_n$alkyl" refers to a single covalent bond ($C_0$) or an alkyl group having from 1 to n carbon atoms; for example "$C_0$-$C_4$alkyl" refers to a single covalent bond or a $C_1$-$C_4$alkyl group. In some instances, a substituent of an alkyl group is specifically indicated. For example, "hydroxyalkyl" refers to an alkyl group substituted with at least one hydroxy substituent.

"Alkylene" refers to a divalent alkyl group, as defined above. $C_1$-$C_2$alkylene is methylene or ethylene; $C_0$-$C_4$alkylene is a single covalent bond or an alkylene group having 1, 2, 3 or carbon atoms; $C_0$-$C_2$alkylene is a single covalent bond or an alkylene group having 1 or 2 carbon atoms.

"Alkenyl" refers to straight or branched chain alkene groups, which comprise at least one unsaturated carbon-carbon double bond. Alkenyl groups include $C_2$-$C_8$alkenyl, $C_2$-$C_6$alkenyl and $C_2$-$C_4$alkenyl groups, which have from 2 to 8, 2 to 6 or 2 to 4 carbon atoms, respectively, such as ethenyl, allyl or isopropenyl. "Alkynyl" refers to straight or branched chain alkyne groups, which have one or more unsaturated carbon-carbon bonds, at least one of which is a triple bond. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, and partially saturated variants of the foregoing, such as cyclohexenyl. Cycloalkyl groups do not comprise an aromatic ring or a heterocyclic ring. Certain cycloalkyl groups are $C_3$-$C_7$cycloalkyl, in which the cycloalkyl group contains a single ring having from 3 to 7 ring members, all of which are carbon. A "($C_3$-$C_8$cycloalkyl)$C_0$-$C_4$alkyl" is a $C_3$-$C_8$cycloalkyl group linked via a single covalent bond or a $C_1$-$C_4$alkylene group.

By "alkoxy," as used herein, is meant an alkyl group as described above attached via an oxygen bridge. Alkoxy groups include $C_1$-$C_6$alkoxy and $C_1$-$C_4$alkoxy groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

Similarly, "alkylthio" refers to an alkyl group as described above attached via a sulfur bridge.

"Alkyl ether" refers to a linear or branched ether substituent (i.e., an alkyl group that is substituted with an alkoxy group). Alkyl ether groups include $C_2$-$C_8$alkyl ether, $C_2$-$C_6$alkyl ether and $C_2$-$C_4$alkyl ether groups, which have 2 to 8, 6 or 4 carbon atoms, respectively. A $C_2$alkyl ether has the structure —$CH_2$—O—$CH_3$.

The term "alkanoyl" refers to an acyl group (e.g., —(C=O)-alkyl), in which carbon atoms are in a linear or branched alkyl arrangement and where attachment is through the carbon of the keto group. Alkanoyl groups have the indicated number of carbon atoms, with the carbon of the keto group being included in the numbered carbon atoms. For example a $C_2$alkanoyl group is an acetyl group having the formula —(C=O)$CH_3$; "$C_1$alkanoyl" refers to —(C=O)H. "$C_1$-$C_6$alkanoyl groups" contain from 1 to 6 carbon atoms.

The term "alkanoyloxy" as used herein refers to an alkanoyl group attached through an oxygen linker (i.e., a group having the general structure —O—C(=O)-alkyl).

Alkanoyloxy groups include, for example, $C_1$-$C_6$alkanoyloxy groups, which have from one to six carbon atoms.

"Alkanoylamino," as used herein, refers to an alkanoyl group attached through an amino linker (i.e., a group having the general structure —N(R)—C(=O)-alkyl), in which R is hydrogen or $C_1$-$C_6$alkyl).

Alkanoylamino groups include, for example, $C_1$-$C_6$alkanoylamino groups, which have from 1 to 6 carbon atoms in the "alkyl" portion (i.e., the carbon of the keto bridge is not included in the indicated number of carbon atoms).

"Alkylsulfonyl" refers to groups of the formula —($SO_2$)-alkyl, in which the sulfur atom is the point of attachment. Alkylsulfonyl groups include $C_1$-$C_6$alkylsulfonyl and $C_1$-$C_4$alkylsulfonyl groups, which have from 1 to 6 or from 1 to 4 carbon atoms, respectively. Methylsulfonyl is one representative alkylsulfonyl group.

"Alkylsulfonylamino" refers to an alkylsulfonyl group attached through an amino linker (i.e., a group having the general structure —N(R)—($SO_2$)-alkyl), in which R is hydrogen or $C_1$-$C_6$alkyl). Alkylsulfonylamino groups include, for example, $C_1$-$C_6$alkylsulfonylamino groups, which have from 1 to 6 carbon atoms.

"Aminosulfonyl" refers to groups of the formula —($SO_2$)—$NH_2$, in which the sulfur atom is the point of attachment. The term "mono- or di-($C_1$-$C_6$alkyl)aminosulfonyl" refers to groups that satisfy the formula —($SO_2$)—$NR_2$, in which the sulfur atom is the point of attachment, and in which one R is $C_1$-$C_6$alkyl and the other R is hydrogen or an independently chosen $C_1$-$C_6$alkyl.

"Alkylamino" refers to a secondary or tertiary amine that has the general structure —NH-alkyl or —N(alkyl)(alkyl), wherein each alkyl is selected independently from alkyl, cycloalkyl and (cycloalkyl)alkyl groups. Such groups include, for example, mono- and di-($C_1$-$C_6$alkyl)amino groups, in which each $C_1$-$C_6$alkyl may be the same or different.

"Alkylaminoalkyl" refers to an alkylamino group linked via an alkylene group (i.e., a group having the general structure -alkylene-NH-alkyl or -alkylene-N(alkyl)(alkyl)) in which each alkyl is selected independently from alkyl, cycloalkyl and (cycloalkyl)alkyl groups. Alkylaminoalkyl groups include, for example, mono- and di-($C_1$-$C_8$alkyl)amino$C_1$-$C_8$alkyl, mono- and di-($C_1$-$C_6$alkyl)amino$C_1$-$C_6$alkyl and mono- and di-($C_1$-$C_6$alkyl)amino$C_1$-$C_4$alkyl. "Mono- or di-($C_1$-$C_6$alkyl)amino$C_0$-$C_6$alkyl" refers to a mono- or di-($C_1$-$C_6$alkyl)amino group linked via a single covalent bond or a $C_1$-$C_6$alkylene group. The following are representative alkylaminoalkyl groups:

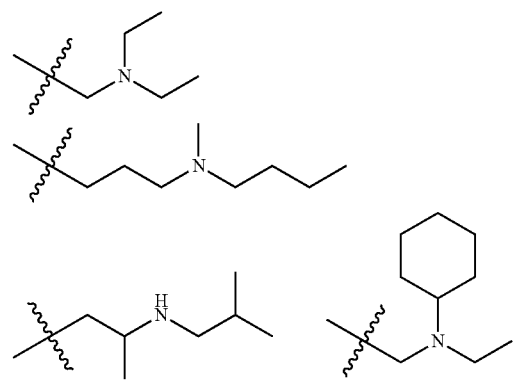

It will be apparent that the definition of "alkyl" as used in the terms "alkylamino" and "alkylaminoalkyl" differs from the definition of "alkyl" used for all other alkyl-containing groups, in the inclusion of cycloalkyl and (cycloalkyl)alkyl groups (e.g., $(C_3-C_7$cycloalkyl)$C_0-C_4$alkyl).

The term "aminocarbonyl" refers to an amide group (i.e., —(C═O)NH$_2$). The term "mono- or di-($C_1$-$C_6$alkyl)aminocarbonyl" refers to groups of the formula —(C═O)—N(R)$_2$, in which the carbonyl is the point of attachment, one R is $C_1$-$C_6$alkyl and the other R is hydrogen or an independently chosen $C_1$-$C_6$alkyl.

The term "halogen" refers to fluorine, chlorine, bromine or iodine.

A "haloalkyl" is an alkyl group that is substituted with 1 or more independently chosen halogens (e.g., "$C_1$-$C_6$haloalkyl" groups have from 1 to 6 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl. Typical haloalkyl groups are trifluoromethyl and difluoromethyl. The term "haloalkoxy" refers to a haloalkyl group as defined above that is linked via an oxygen bridge.

A dash ("-") that is not between two letters or symbols is used to indicate a point of attachment for a substituent. For example, —CONH$_2$ is attached through the carbon atom.

A "heteroaryl" is an aromatic group in which at least one aromatic ring comprises at least one heteroatom selected from N, O and S. Heteroaryls include, for example, 5- and 6-membered heteroaryls such as imidazole, furan, furazan, isothiazole, isoxazole, oxadiazole, oxazole, pyrazine, pyrazole, pyridazine, pyridine, pyrimidine, tetrazole, thiazole and thiophene.

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

Groups that are "optionally substituted" are unsubstituted or are substituted by other than hydrogen at one or more available positions, typically 1, 2, 3, 4 or 5 positions, by one or more suitable groups (which may be the same or different). Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents). Other optionally substituted groups are substituted with at least one substituent (e.g., substituted with from 1 to 2, 3 or 4 independently selected substituents).

The terms "VR1" and "capsaicin receptor" are used interchangeably herein to refer to a type 1 vanilloid receptor. Unless otherwise specified, these terms encompass both rat and human VR1 receptors (e.g., GenBank Accession Numbers AF327067, AJ277028 and NM_018727; sequences of certain human VR1 cDNAs and the encoded amino acid sequences are provided in U.S. Pat. No. 6,482,611), as well as homologues thereof found in other species.

A "VR1 modulator," also referred to herein as a "modulator," is a compound that modulates VR1 activation and/or VR1-mediated signal transduction. VR1 modulators specifically provided herein are compounds of Formula A, and pharmaceutically acceptable salts, hydrates and esters thereof. Certain preferred VR1 modulators are not vanilloids. A VR1 modulator may be a VR1 agonist or antagonist. Certain modulators bind to VR1 with a $K_i$ that is less than 1 micromolar, preferably less than 500 nanomolar, 100 nanomolar, 10 nanomolar or 1 nanomolar. A representative assay for determining $K_i$ at VR1 is provided in Example 5, herein.

A modulator is considered an "antagonist" if it detectably inhibits vanilloid ligand binding to VR1 and/or VR1-mediated signal transduction (using, for example, the representative assay provided in Example 6); in general, such an antagonist inhibits VR1 activation with a $IC_{50}$ value of less than 1 micromolar, preferably less than 500 nanomolar, and more preferably less than 100 nanomolar, 10 nanomolar or 1 nanomolar within the assay provided in Example 6. VR1 antagonists include neutral antagonists and inverse agonists.

An "inverse agonist" of VR1 is a compound that reduces the activity of VR1 below its basal activity level in the absence of added vanilloid ligand. Inverse agonists of VR1 may also inhibit the activity of vanilloid ligand at VR1 and/or binding of vanilloid ligand to VR1. The basal activity of VR1, as well as the reduction in VR1 activity due to the presence of VR1 antagonist, may be determined from a calcium mobilization assay, such as the assay of Example 6.

A "neutral antagonist" of VR1 is a compound that inhibits the activity of vanilloid ligand at VR1, but does not significantly change the basal activity of the receptor (i.e., within a calcium mobilization assay as described in Example 6 performed in the absence of vanilloid ligand, VR1 activity is reduced by no more than 10%, preferably by no more than 5%, and more preferably by no more than 2%; most preferably, there is no detectable reduction in activity). Neutral antagonists of VR1 may inhibit the binding of vanilloid ligand to VR1.

As used herein a "capsaicin receptor agonist" or "VR1 agonist" is a compound that elevates the activity of the receptor above the basal activity level of the receptor (i.e., enhances VR1 activation and/or VR1-mediated signal transduction). Capsaicin receptor agonist activity may be identified using the representative assay provided in Example 6. In general, such an agonist has an $EC_{50}$ value of less than 1 micromolar, preferably less than 500 nanomolar, and more preferably less than 100 nanomolar or 10 nanomolar within the assay provided in Example 6.

A "vanilloid" is any compound that comprises a phenyl ring with two oxygen atoms bound to adjacent ring carbon atoms (one of which carbon atom is located para to the point of attachment of a third moiety that is bound to the phenyl ring). Capsaicin is a representative vanilloid. A "vanilloid ligand" is a vanilloid that binds to VR1 with a $K_i$ (determined as described herein) that is no greater than 10 μM. Vanilloid ligand agonists include capsaicin, olvanil, N-arachidonoyldopamine and resiniferatoxin (RTX). Vanilloid ligand antagonists include capsazepine and iodo-resiniferatoxin.

A "therapeutically effective amount" (or dose) is an amount that, upon administration to a patient, results in a discernible patient benefit (e.g., provides detectable relief from at least one condition being treated). Such relief may be detected using any appropriate criteria, including alleviation of one or more symptoms such as pain. A therapeutically effective amount or dose generally results in a concentration of compound in a body fluid (such as blood, plasma, serum, CSF, synovial fluid, lymph, cellular interstitial fluid, tears or urine) that is sufficient to alter the binding of vanilloid ligand to VR1 in vitro (using the assay provided in Example 5) and/or VR1-mediated signal transduction (using an assay provided in Example 6). It will be apparent that the discernible patient benefit may be apparent after administration of a single dose, or may become apparent following repeated administration of the therapeutically effective dose according to a predetermined regimen, depending upon the indication for which the compound is administered.

By "statistically significant," as used herein, is meant results varying from control at the $p<0.1$ level of significance as measured using a standard parametric assay of statistical significance such as a student's T test.

A "patient" is any individual treated with a compound provided herein. Patients include humans, as well as other animals such as companion animals (e.g., dogs and cats) and livestock. Patients may be experiencing one or more symptoms of a condition responsive to capsaicin receptor modulation (e.g., pain, exposure to vanilloid ligand, itch, urinary incontinence, overactive bladder, menopause symptoms, respiratory disorders, cough and/or hiccup), or may be free of such symptom(s) (i.e., treatment may be prophylactic in a patient considered at risk for the development of such symptoms).

2-Phenoxy Pyrimidinone Analogues

As noted above, the present invention provides 2-phenoxy pyrimidinone analogues of Formula A. Within certain aspects, such compounds are VR1 modulators that may be used in a variety of contexts, including in the treatment of pain (e.g., neuropathic or peripheral nerve-mediated pain); exposure to capsaicin; exposure to acid, heat, light, tear gas, air pollutants (such as, for example, tobacco smoke), infectious agents (including viruses, bacteria and yeast), pepper spray or related agents; respiratory conditions such as asthma or chronic obstructive pulmonary disease; itch; urinary incontinence or overactive bladder; menopause symptoms; cough or hiccup; and/or obesity. Such compounds may also be used within in vitro assays (e.g., assays for receptor activity), as probes for detection and localization of VR1 and as standards in ligand binding and VR1-mediated signal transduction assays.

It has been found, within the context of the present invention, that the 2-phenoxy pyrimidinone analogues provided herein exhibit an unexpectedly high VR1-modulating activity due, at least in part, to the phenoxy moiety of Formula A and Formula I.

As noted above,

represents a fused, optionally substituted 5- or 6-membered heteroaryl in which 1, 2 or 3 ring members are heteroatoms independently chosen from O, N and S, and the remaining ring members are carbon. Within certain embodiments,

is substituted with from 0 to 2 substituents independently chosen from $C_1$-$C_6$alkyl, $(C_3$-$C_7$cycloalkyl)$C_0$-$C_2$alkyl and $C_1$-$C_6$haloalkyl. Within further embodiments,

is substituted with from 0 to 2 substituents independently chosen from $C_1$-$C_4$alkyl, $(C_3$-$C_5$cycloalkyl)$C_0$-$C_2$alkyl and $C_1$-$C_4$haloalkyl.

Within certain embodiments,

is a 5-membered heteroaryl that is substituted with from 0 to 2 substituents independently chosen from $C_1$-$C_4$alkyl, $(C_3$-$C_5$cycloalkyl)$C_0$-$C_2$alkyl and $C_1$-$C_4$haloalkyl. In other embodiments,

is a 5-membered heteroaryl represented by any of the formulae:

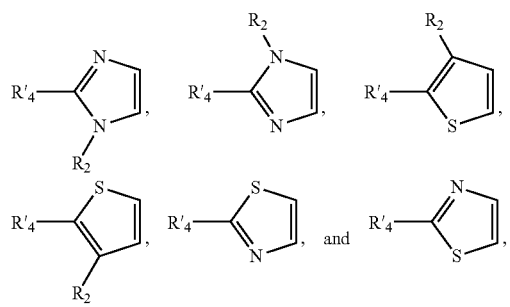

in which $R'_4$ is hydrogen, $C_1$-$C_4$alkyl, $(C_3$-$C_5$cycloalkyl)$C_0$-$C_2$alkyl, $C_1$-$C_4$haloalkyl, $C_1$-$C_4$hydroxyalkyl, $C_1$-$C_4$alkoxy, $C_1$-$C_4$alkanoylamino or $C_1$-$C_4$alkylsulfonylamino. Representative such groups include, for example,

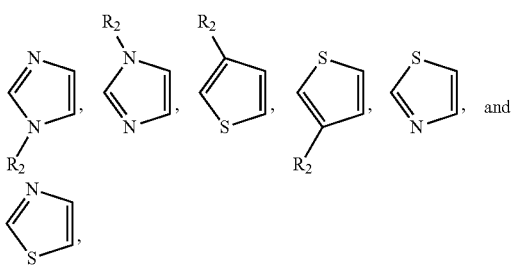 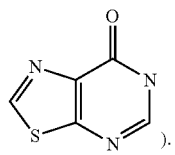, and

, in which $R_2$ is, for example, hydrogen, cyano, aryl, heteroaryl, halogen, $C_1$-$C_4$alkyl, $C_1$-$C_4$haloalkyl or $C_3$-$C_5$cycloalkyl. Within certain embodiments,

is

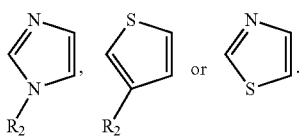

It will be apparent that the orientation of such

moieties is intended to be retained as shown (e.g., if

is

then the bicyclic core

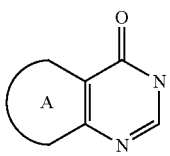

is

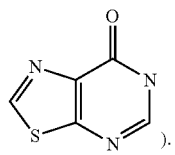.

Within other embodiments,

is a 6-membered heteroaryl that is substituted with from 0 to 3 substituents independently chosen from hydroxy, $C_1$-$C_6$alkyl, $(C_3$-$C_7$cycloalkyl)$C_0$-$C_2$alkyl, $C_1$-$C_6$haloalkyl, $C_1$-$C_6$hydroxyalkyl, $C_1$-$C_6$alkoxy, mono-($C_1$-$C_6$alkyl) amino, $C_1$-$C_6$alkanoylamino or $C_1$-$C_6$alkylsulfonylamino. Representative such groups include, for example,

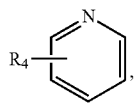

wherein $R_4$ represents from 0 to 3, preferably from 1 to 3, substituents independently chosen from hydroxy, $C_1$-$C_4$alkyl, $(C_3$-$C_5$cycloalkyl)$C_0$-$C_2$alkyl, $C_1$-$C_4$haloalkyl, $C_1$-$C_4$hydroxyalkyl, $C_1$-$C_4$alkoxy, mono-($C_1$-$C_4$alkyl) amino, $C_1$-$C_4$alkanoylamino or $C_1$-$C_4$alkylsulfonylamino.

The variable $R_1$, within certain embodiments, represents from 0 to 3, preferably from 1 to 3, substituents independently chosen from halogen, cyano, $C_1$-$C_4$alkyl and $C_1$-$C_4$haloalkyl. For example, $R_1$ represents exactly one substituent (e.g., at the para position of the ring Ar) within certain such compounds. Within other such compounds, at least one substituent represented by $R_1$ is a halogen or CN; such substituent is located at the para position of a 6-membered Ar moiety within certain such compounds. It will be apparent that, within Formula I, the para position refers to the position para to the point of attachment of the Ar moiety to the pyrimidinone core; that is, the 4-position of the phenyl ring that results when X is CH, and the 6-position of the pyridin-3-yl ring that results when X is N.

Within certain embodiments, $R_3$ represents from 1 to 3 substituents independently chosen from halogen, cyano, $C_1$-$C_4$alkyl, $C_1$-$C_4$haloalkyl and $C_1$-$C_4$alkoxy.

In certain embodiments, compounds of Formula I further satisfy one of Formulas II-VII:

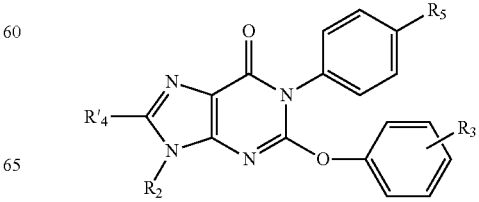

Formula II

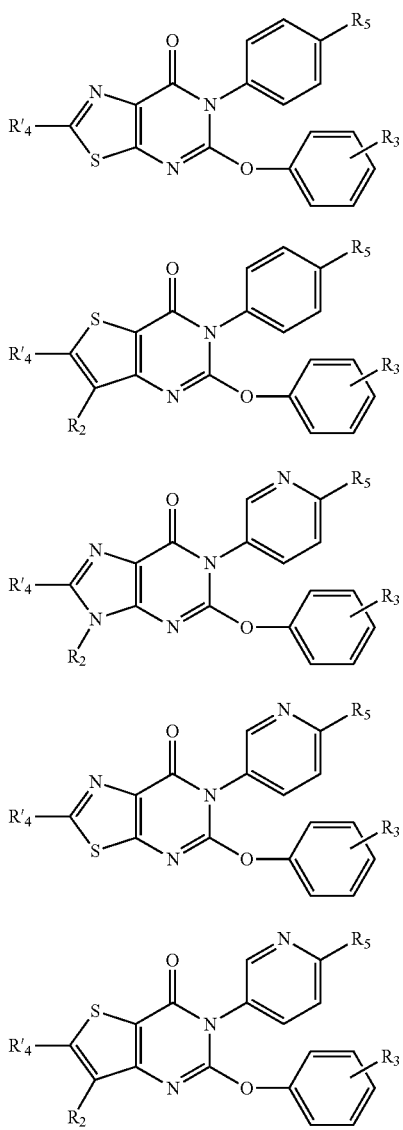

Formula III

Formula IV

Formula V

Formula VI

Formula VII in which $R_2$ is hydrogen, $C_1$-$C_4$alkyl, $C_1$-$C_4$haloalkyl or $C_3$-$C_5$cycloalkyl; $R_3$ represents from 1 to 3 substituents independently chosen from halogen, cyano, $C_1$-$C_4$alkyl, $C_1$-$C_4$haloalkyl and $C_1$-$C_4$alkoxy; $R'_4$ is hydrogen, $C_1$-$C_4$alkyl, ($C_3$-$C_5$cycloalkyl)$C_0$-$C_2$alkyl, $C_1$-$C_4$haloalkyl, $C_1$-$C_4$hydroxyalkyl, $C_1$-$C_4$alkoxy, $C_1$-$C_4$alkanoylamino or $C_1$-$C_4$alkylsulfonylamino; and $R_5$ is halogen or CN. In certain embodiments of Formulas II-VII, $R'_4$ is H (i.e. such compounds further satisfy one of Formulas III-VIIa:

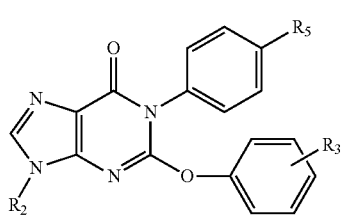

Formula IIa

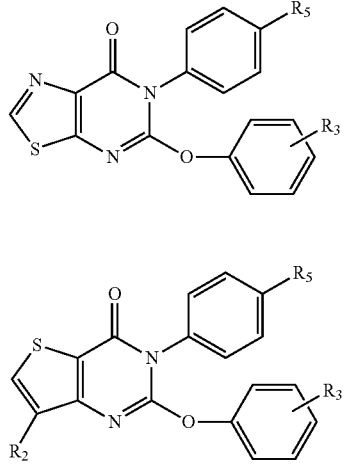

Formula IIIa

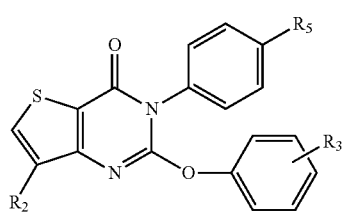

Formula IVa

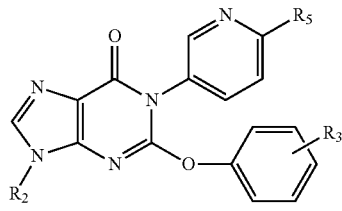

Formula Va

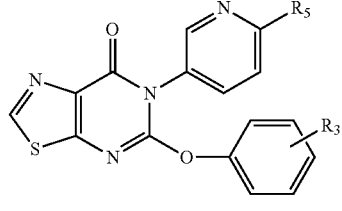

Formula VIa

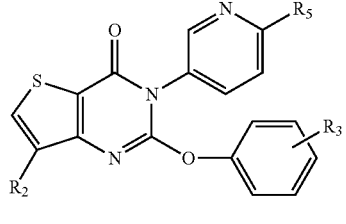

Formula VIIa in which variables are as described for Formulas II-VII. Within further embodiments, compounds of Formula I further satisfy Formula VIII or IX:

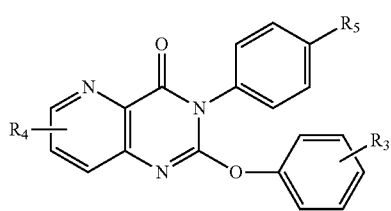

Formula VIII

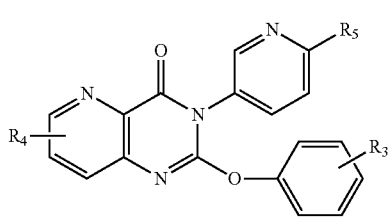

Formula IX in which $R_3$ represents from 1 to 3 substituents independently chosen from halogen, cyano, $C_1$-$C_4$alkyl, $C_1$-$C_4$haloalkyl and $C_1$-$C_4$alkoxy; $R_4$ represents from 0 to 2 substituents independently chosen from hydroxy, $C_1$-$C_4$alkyl, ($C_3$-$C_5$cycloalkyl) $C_0$-$C_2$alkyl, $C_1$-$C_4$haloalkyl, $C_1$-$C_4$hydroxyalkyl, $C_1$-$C_4$alkoxy, mono-($C_1$-$C_4$alkyl)amino, $C_1$-$C_4$alkanoylamino or $C_1$-$C_4$alkylsulfonylamino; and $R_5$ is halogen or CN.

Representative 2-phenoxy pyrimidinone analogues and intermediates provided herein include, but are not limited to, those specifically described in Examples 1-3. It will be apparent that the specific compounds recited herein are representative only, and are not intended to limit the scope of the present invention. Further, as noted above, all compounds of the present invention may be present as a free acid or base, or as a pharmaceutically acceptable salt. In addition, other forms such as hydrates and prodrugs of such compounds are specifically contemplated by the present invention.

Within certain aspects of the present invention, 2-phenoxy pyrimidinone analogues provided herein detectably alter (modulate) VR1 activity, as determined using an in vitro VR1 functional assay such as a calcium mobilization assay. As an initial screen for such activity, a VR1 ligand binding assay may be used. References herein to a "VR1 ligand binding assay" are intended to refer to a standard in vitro receptor binding assay such as that provided in Example 5, and a "calcium mobilization assay" (also referred to herein as a "signal transduction assay") may be performed as described in Example 6. Briefly, to assess binding to VR1, a competition assay may be performed in which a VR1 preparation is incubated with labeled (e.g., $^{125}$I or $^3$H) compound that binds to VR1 (e.g., a capsaicin receptor agonist such as RTX) and unlabeled test compound. Within the assays provided herein, the VR1 used is preferably mammalian VR1, more preferably human or rat VR1. The receptor may be recombinantly expressed or naturally expressed. The VR1 preparation may be, for example, a membrane preparation from HEK293 or CHO cells that recombinantly express human VR1. Incubation with a compound that detectably modulates vanilloid ligand binding to VR1 results in a decrease or increase in the amount of label bound to the VR1 preparation, relative to the amount of label bound in the absence of the compound. This decrease or increase may be used to determine the $K_i$ at VR1 as described herein. In general, compounds that decrease the amount of label bound to the VR1 preparation within such an assay are preferred.

Certain VR1 modulators provided herein detectably modulate VR1 activity at nanomolar (i.e., submicromolar) concentrations, at subnanomolar concentrations, or at concentrations below 100 picomolar, 20 picomolar, 10 picomolar or 5 picomolar.

As noted above, compounds that are VR1 antagonists are preferred within certain embodiments. $IC_{50}$ values for such compounds may be determined using a standard in vitro VR1-mediated calcium mobilization assay, as provided in Example 6. Briefly, cells expressing capsaicin receptor are contacted with a compound of interest and with an indicator of intracellular calcium concentration (e.g., a membrane permeable calcium sensitivity dye such as Fluo-3 or Fura-2 (Molecular Probes, Eugene, Oreg.), each of which produce a fluorescent signal when bound to $Ca^{++}$). Such contact is preferably carried out by one or more incubations of the cells in buffer or culture medium comprising either or both of the compound and the indicator in solution. Contact is maintained for an amount of time sufficient to allow the dye to enter the cells (e.g., 1-2 hours). Cells are washed or filtered to remove excess dye and are then contacted with a vanilloid receptor agonist (e.g., capsaicin, RTX or olvanil), typically at a concentration equal to the $EC_{50}$ concentration, and a fluorescence response is measured. When agonist-contacted cells are contacted with a compound that is a VR1 antagonist the fluorescence response is generally reduced by at least 20%, preferably at least 50% and more preferably at least 80%, as compared to cells that are contacted with the agonist in the absence of test compound. The $IC_{50}$ for VR1 antagonists provided herein is preferably less than 1 micromolar, less than 100 nM, less than 10 nM or less than 1 nM. In certain embodiments, VR1 antagonists provided herein exhibit no detectable agonist activity an in vitro assay of capsaicin receptor agonism at a concentration of compound equal to the $IC_{50}$. Certain such antagonists exhibit no detectable agonist activity an in vitro assay of capsaicin receptor agonism at a concentration of compound that is 100-fold higher than the $IC_{50}$.

In other embodiments, compounds that are capsaicin receptor agonists are preferred. Capsaicin receptor agonist activity may generally be determined as described in Example 6. When cells are contacted with 1 micromolar of a compound that is a VR1 agonist, the fluorescence response is generally increased by an amount that is at least 30% of the increase observed when cells are contacted with 100 nM capsaicin. The $EC_{50}$ for VR1 agonists provided herein is preferably less than 1 micromolar, less than 100 nM or less than 10 nM.

VR1 modulating activity may also, or alternatively, be assessed using a cultured dorsal root ganglion assay as provided in Example 7 and/or an in vivo pain relief assay as provided in Example 8. VR1 modulators provided herein preferably have a statistically significant specific effect on VR1 activity within one or more functional assays provided herein.

Within certain embodiments, VR1 modulators provided herein do not substantially modulate ligand binding to other cell surface receptors, such as EGF receptor tyrosine kinase or the nicotinic acetylcholine receptor. In other words, such modulators do not substantially inhibit activity of a cell surface receptor such as the human epidermal growth factor (EGF) receptor tyrosine kinase or the nicotinic acetylcholine receptor (e.g., the $IC_{50}$ or $IC_{40}$ at such a receptor is preferably greater than 1 micromolar, and most preferably greater than 10 micromolar). Preferably, a modulator does not detectably inhibit EGF receptor activity or nicotinic acetylcholine receptor activity at a concentration of 0.5 micromolar, 1 micromolar or more preferably 10 micromolar. Assays for determining cell surface receptor activity are commercially available, and include the tyrosine kinase assay kits available from Panvera (Madison, Wis.).

In certain embodiments, preferred VR1 modulators are non-sedating. In other words, a dose of VR1 modulator that is twice the minimum dose sufficient to provide analgesia in an animal model for determining pain relief (such as a model provided in Example 8, herein) causes only transient (i.e., lasting for no more than ½ the time that pain relief lasts) or preferably no statistically significant sedation in an animal model assay of sedation (using the method described by Fitzgerald et al. (1988) *Toxicology* 49(2-3):433-9). Preferably, a dose that is five times the minimum dose sufficient to provide analgesia does not produce statistically significant sedation. More preferably, a VR1 modulator provided herein does not produce sedation at intravenous doses of less than 25 mg/kg (preferably less than 10 mg/kg) or at oral doses of less than 140 mg/kg (preferably less than 50 mg/kg, more preferably less than 30 mg/kg).

If desired, compounds provided herein may be evaluated for certain pharmacological properties including, but not limited to, oral bioavailability (preferred compounds are orally bioavailable to an extent allowing for therapeutically effective concentrations of the compound to be achieved at oral doses of less than 140 mg/kg, preferably less than 50 mg/kg, more preferably less than 30 mg/kg, even more preferably less than 10 mg/kg, still more preferably less than 1 mg/kg and most preferably less than 0.1 mg/kg), toxicity (a preferred compound is nontoxic when a therapeutically effective amount is administered to a subject), side effects (a preferred compound produces side effects comparable to placebo when a therapeutically effective amount of the compound is administered to a subject), serum protein binding and in vitro and in vivo half-life (a preferred compound exhibits an in vivo half-life allowing for Q.I.D. dosing, preferably T.I.D. dosing, more preferably B.I.D. dosing, and most preferably once-a-day dosing). In addition, differential penetration of the blood brain barrier may be desirable for VR1 modulators used to treat pain by modulating CNS VR1 activity such that total daily oral doses as described above provide such modulation to a therapeutically effective extent, while low brain levels of VR1 modulators used to treat peripheral nerve mediated pain may be preferred (i.e., such doses do not provide brain (e.g., CSF) levels of the compound sufficient to significantly modulate VR1 activity). Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound (e.g., intravenously). Serum protein binding may be predicted from albumin binding assays. Compound half-life is inversely proportional to the frequency of dosage of a compound. In vitro half-lives of compounds may be predicted from assays of microsomal half-life as described, for example, within Example 7 of U.S. Patent Application Publication Number 2005/0070547.

As noted above, preferred compounds provided herein are nontoxic. In general, the term "nontoxic" shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, or (4) does not cause substantial release of liver enzymes.

As used herein, a compound that does not substantially inhibit cellular ATP production is a compound that satisfies the criteria set forth in Example 8 of U.S. Patent Application Publication Number 2005/0070547. In other words, cells treated as described therein with 100 µM of such a compound exhibit ATP levels that are at least 50% of the ATP levels detected in untreated cells. In more highly preferred embodiments, such cells exhibit ATP levels that are at least 80% of the ATP levels detected in untreated cells.

A compound that does not significantly prolong heart QT intervals is a compound that does not result in a statistically significant prolongation of heart QT intervals (as determined by electrocardiography) in guinea pigs, minipigs or dogs upon administration of a dose that yields a serum concentration equal to the $EC_{50}$ or $IC_{50}$ for the compound. In certain preferred embodiments, a dose of 0.01, 0.05, 0.1, 0.5, 1, 5, 10, 40 or 50 mg/kg administered parenterally or orally does not result in a statistically significant prolongation of heart QT intervals.

A compound does not cause substantial liver enlargement if daily treatment of laboratory rodents (e.g., mice or rats) for 5-10 days with a dose that yields a serum concentration equal to the $EC_{50}$ or $IC_{50}$ for the compound results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05. 0.1, 0.5, 1, 5, 10, 40 or 50 mg/kg administered parenterally or orally.

Similarly, a compound does not promote substantial release of liver enzymes if administration of twice the minimum dose that yields a serum concentration equal to the $EC_{50}$ or $IC_{50}$ at VR1 for the compound does not elevate serum levels of ALT, LDH or AST in laboratory animals (e.g., rodents) by more than 100% over matched mock-treated controls. In more highly preferred embodiments, such doses do not elevate such serum levels by more than 75% or 50% over matched controls. Alternatively, a compound does not promote substantial release of liver enzymes if, in an in vitro hepatocyte assay, concentrations (in culture media or other such solutions that are contacted and incubated with hepatocytes in vitro) that are equal to the $EC_{50}$ or $IC_{50}$ for the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the $EC_{50}$ or $IC_{50}$ for the compound.

In other embodiments, certain preferred compounds do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the $EC_{50}$ or $IC_{50}$ at VR1 for the compound.

Certain preferred compounds are not clastogenic (e.g., as determined using a mouse erythrocyte precursor cell micronucleus assay, an Ames micronucleus assay, a spiral micronucleus assay or the like) at a concentration equal the $EC_{50}$ or $IC_{50}$ for the compound. In other embodiments, certain preferred compounds do not induce sister chromatid exchange (e.g., in Chinese hamster ovary cells) at such concentrations.

For detection purposes, as discussed in more detail below, VR1 modulators provided herein may be isotopically-labeled or radiolabeled. For example, compounds may have one or more atoms replaced by an atom of the same element having an atomic mass or mass number different from the atomic mass or mass number usually found in nature. Examples of isotopes that can be present in the compounds provided herein include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl. In addition, substitution with heavy isotopes such as deuterium (i.e., $^2$H) can afford certain therapeutic advantages resulting from greater metabolic stability, for example increased in vivo half-life or reduced dosage requirements and, hence, may be preferred in some circumstances.

Preparation of 2-Phenoxy Pyrimidinone Analogues

2-Phenoxy pyrimidinone analogues may generally be prepared using standard synthetic methods. Starting materials are commercially available from suppliers such as Sigma-Aldrich Corp. (St. Louis, Mo.), or may be synthesized from commercially available precursors using established protocols. By way of example, a synthetic route similar to that shown in any of the following Schemes may be used, together with synthetic methods known in the art of synthetic organic chemistry. Each variable in the following schemes refers to any group consistent with the description of the compounds provided herein.

Certain abbreviations used in the following Schemes and elsewhere herein include:

CDCl$_3$ deuterated chloroform
δ chemical shift
DCM dichloromethane
DMAP 4-dimethylaminopyridine
DMF dimethylformamide
DMSO dimethylsulfoxide
DPPF 1,1'-bis(diphenylphosphino)ferrocene
Et ethyl
EtOAc ethyl acetate
EtOH ethanol
h hour(s)
$^1$H NMR proton nuclear magnetic resonance
HPLC high pressure liquid chromatography
Hz hertz
KO$^t$Bu potassium tert-butoxide
min minute(s)
MS mass spectrometry
(M+1) mass+1
Pd$_2$(dba)$_3$ tris(dibenzylidineacetone)dipalladium(0)
RT room temperature
TFA trifluoroacetic acid

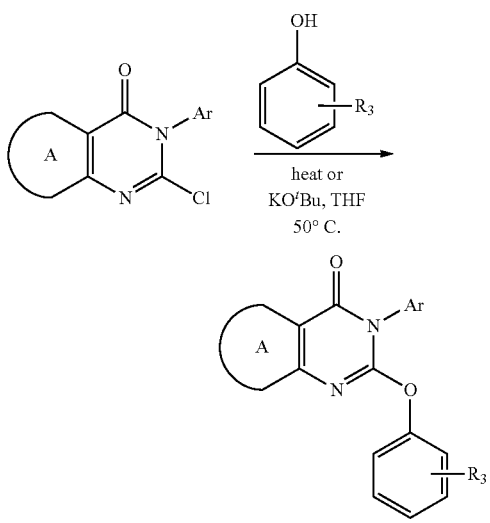

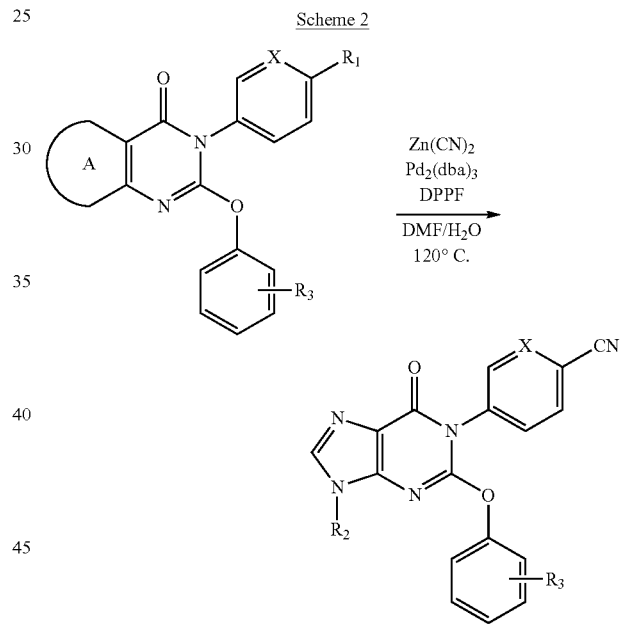

$R_1$ = Br or Cl

Scheme 1

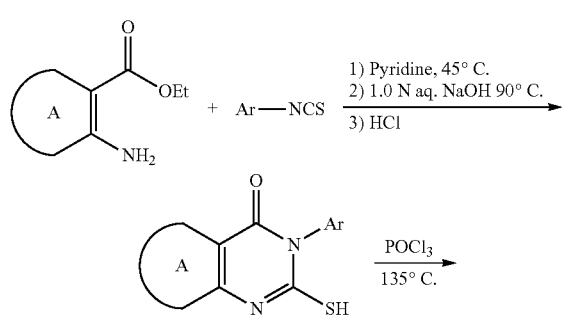

Scheme 3

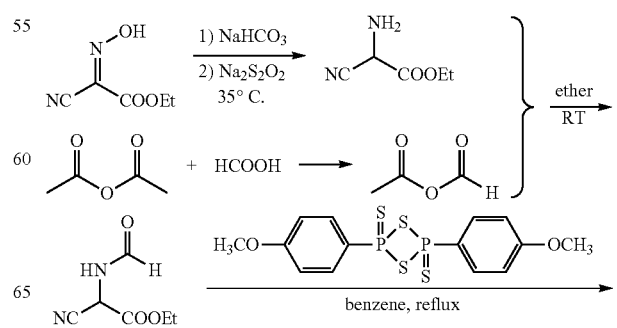

-continued
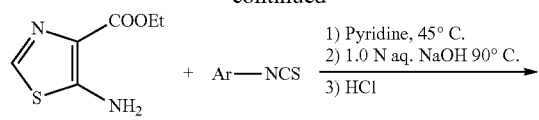
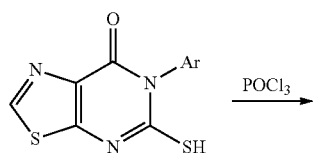
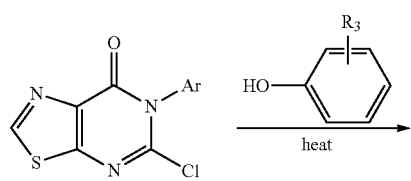
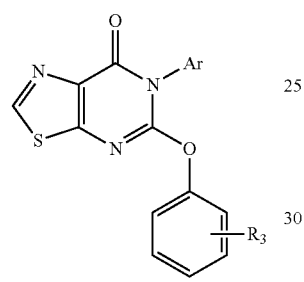
Scheme 4
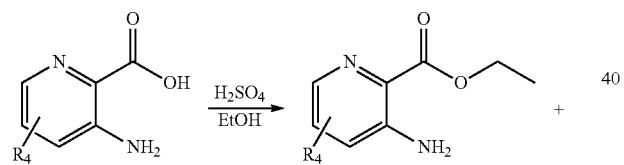
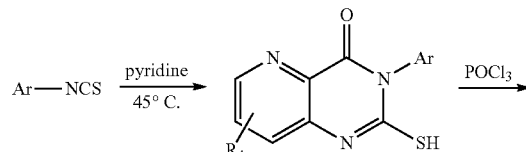
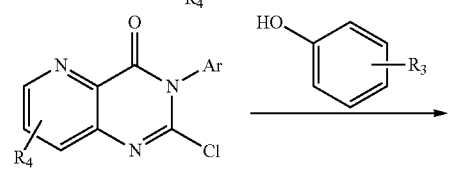
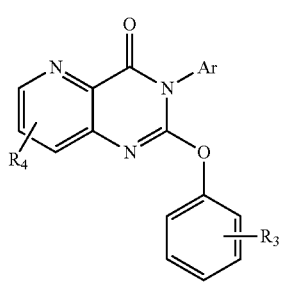
Scheme 5
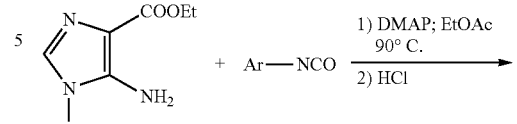
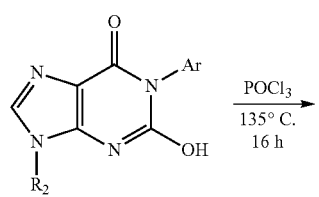
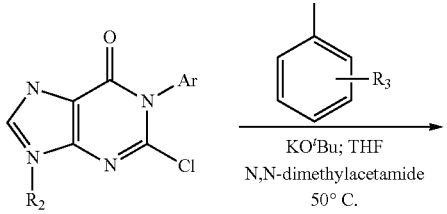
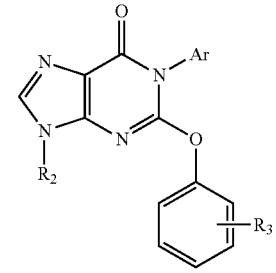
Scheme 6
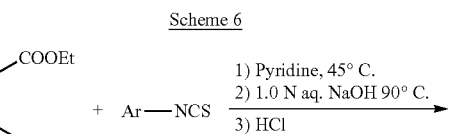
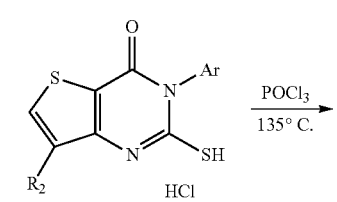
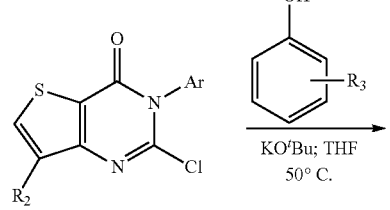

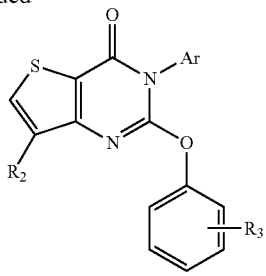

In certain embodiments, a compound provided herein may contain one or more asymmetric carbon atoms, so that the compound can exist in different stereoisomeric forms. Such forms can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

Compounds may be radiolabeled by carrying out their synthesis using precursors comprising at least one atom that is a radioisotope. Each radioisotope is preferably carbon (e.g., $^{14}C$), hydrogen (e.g., $^{3}H$), sulfur (e.g., $^{35}S$), or iodine (e.g., $^{125}I$). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

Pharmaceutical Compositions

The present invention also provides pharmaceutical compositions comprising one or more compounds provided herein, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. In addition, other active ingredients may (but need not) be included in the pharmaceutical compositions provided herein.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions suitable for oral use are preferred. Such compositions include, for example, tablets, troches, lozenges, aqueous or oily suspensions, dispersible powders or granules, emulsion, hard or soft capsules, or syrups or elixirs. Within yet other embodiments, pharmaceutical compositions may be formulated as a lyophilizate. Formulation for topical administration may be preferred for certain conditions (e.g., in the treatment of skin conditions such as burns or itch). Formulation for direct administration into the bladder (intravesicular administration) may be preferred for treatment of urinary incontinence and overactive bladder.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). Tablets may be formed using standard techniques, including dry granulation, direct compression and wet granulation. The tablets may be uncoated or they may be coated by known techniques.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with suitable excipients, such as suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, such as ethyl or n-propyl p-hydroxybenzoate, one or more coloring agents, one or more flavoring agents, and/or one or more sweetening agents, such as sucrose or saccharin.

Oily suspensions may be formulated by suspending the active ingredient(s) in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be formulated as oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and *Remington: The Science and Practice of Pharmacy*, 21$^{st}$ ed., Lippincott Williams & Wilkins, Philadelphia, Pa. (2005). Formulations may comprise microcapsules, such as hydroxymethylcellulose or gelatin-microcapsules, liposomes, albumin microspheres, microemulsions, nanoparticles or nanocapsules.

A topical formulation may be prepared in any of a variety of physical forms including, for example, solids, pastes, creams, foams, lotions, gels, powders, aqueous liquids and emulsions. The physical appearance and viscosity of such pharmaceutically acceptable forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations. Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included a topical formulation include, but are not limited to, abrasives, absorbents, anti-caking agents, anti-foaming agents, anti-static agents, astringents (e.g., witch hazel, alcohol and herbal extracts such as chamomile extract), binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quaternium 52 (1.0%); propylene glycol (2.0%); ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying (including mist, aerosol or foam spraying); dropper application; sprinkling; soaking; and rinsing.

A pharmaceutical composition may be prepared as a sterile injectible aqueous or oleaginous suspension. The compound(s) provided herein, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions, and adjuvants such as local anesthetics, preservatives and/or buffering agents can be dissolved in the vehicle.

Pharmaceutical compositions may also be formulated as suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Pharmaceutical compositions may be formulated for release at a pre-determined rate. Instantaneous release may be achieved, for example, via sublingual administration (i.e., administration by mouth in such a way that the active ingredient(s) are rapidly absorbed via the blood vessels under the tongue rather than via the digestive tract). Controlled release formulations (i.e., formulations such as a capsule, tablet or coated tablet that slows and/or delays release of active ingredient(s) following administration) may be administered by, for example, oral, rectal or subcutaneous implantation, or by implantation at a target site. In general, a controlled release formulation comprises a matrix and/or coating that delays disintegration and absorption in the gastrointestinal tract (or implantation site) and thereby provides a delayed action or a sustained action over a longer period. One type of controlled-release formulation is a sustained-release formulation, in which at least one active ingredient is continuously released over a period of time at a constant rate. Preferably, the therapeutic agent is released at such a rate that blood (e.g., plasma) concentrations are maintained within the therapeutic range, but below toxic levels, over a period of time that is at least 4 hours, preferably at least 8 hours, and more preferably at least 12 hours. Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

Controlled release may be achieved by combining the active ingredient(s) with a matrix material that itself alters release rate and/or through the use of a controlled-release coating. The release rate can be varied using methods well known in the art, including (a) varying the thickness or composition of coating, (b) altering the amount or manner of addition of plasticizer in a coating, (c) including additional ingredients, such as release-modifying agents, (d) altering the composition, particle size or particle shape of the matrix, and (e) providing one or more passageways through the coating. The amount of modulator contained within a sustained release formulation depends upon, for example, the method of administration (e.g., the site of implantation), the rate and expected duration of release and the nature of the condition to be treated or prevented.

The matrix material, which itself may or may not serve a controlled-release function, is generally any material that supports the active ingredient(s). For example, a time delay material such as glyceryl monosterate or glyceryl distearate may be employed. Active ingredient(s) may be combined with matrix material prior to formation of the dosage form (e.g., a tablet). Alternatively, or in addition, active ingredient(s) may be coated on the surface of a particle, granule, sphere, microsphere, bead or pellet that comprises the matrix material. Such coating may be achieved by conventional means, such as by dissolving the active ingredient(s) in water or other suitable solvent and spraying. Optionally, additional ingredients are added prior to coating (e.g., to assist binding of the active ingredient(s) to the matrix material or to color the solution). The matrix may then be coated with a barrier agent prior to application of controlled-release coating. Multiple coated matrix units may, if desired, be encapsulated to generate the final dosage form.

In certain embodiments, a controlled release is achieved through the use of a controlled release coating (i.e., a coating that permits release of active ingredient(s) at a controlled rate in aqueous medium). The controlled release coating should be a strong, continuous film that is smooth, capable of supporting pigments and other additives, non-toxic, inert and tack-free. Coatings that regulate release of the modulator include pH-independent coatings, pH-dependent coatings (which may be used to release modulator in the stomach) and enteric coatings (which allow the formulation to pass intact through the stomach and into the small intestine, where the coating dissolves and the contents are absorbed by the body). It will be apparent that multiple coatings may be employed (e.g., to allow release of a portion of the dose in the stomach and a portion further along the gastrointestinal tract). For example, a portion of active ingredient(s) may be coated over an enteric coating, and thereby released in the stomach, while the remainder of active ingredient(s) in the matrix core is protected by the enteric coating and released further down the GI tract. pH dependent coatings include, for example, shellac, cellulose acetate phthalate, polyvinyl acetate phthalate, hydroxypropylmethylcellulose phthalate, methacrylic acid ester copolymers and zein.

In certain embodiments, the coating is a hydrophobic material, preferably used in an amount effective to slow the hydration of the gelling agent following administration. Suitable hydrophobic materials include alkyl celluloses (e.g., ethylcellulose or carboxymethylcellulose), cellulose ethers, cellulose esters, acrylic polymers (e.g., poly(acrylic acid), poly(methacrylic acid), acrylic acid and methacrylic acid copolymers, methyl methacrylate copolymers, ethoxy ethyl methacrylates, cyanoethyl methacrylate, methacrylic acid alkamide copolymer, poly(methyl methacrylate), polyacrylamide, ammonio methacrylate copolymers, aminoalkyl methacrylate copolymer, poly(methacrylic acid anhydride) and glycidyl methacrylate copolymers) and mixtures of the foregoing. Representative aqueous dispersions of ethylcellulose include, for example, AQUACOAT® (FMC Corp., Philadelphia, Pa.) and SURELEASE® (Colorcon, Inc., West Point, Pa.), both of which can be applied to the substrate according to the manufacturer's instructions. Representative acrylic polymers include, for example, the various EUDRAGIT® (Rohm America, Piscataway, N.J.) polymers, which may be used singly or in combination depending on the desired release profile, according to the manufacturer's instructions.

The physical properties of coatings that comprise an aqueous dispersion of a hydrophobic material may be improved by the addition or one or more plasticizers. Suitable plasticizers for alkyl celluloses include, for example, dibutyl sebacate, diethyl phthalate, triethyl citrate, tributyl citrate and triacetin. Suitable plasticizers for acrylic polymers include, for example, citric acid esters such as triethyl citrate and tributyl citrate, dibutyl phthalate, polyethylene glycols, propylene glycol, diethyl phthalate, castor oil and triacetin.

Controlled-release coatings are generally applied using conventional techniques, such as by spraying in the form of an aqueous dispersion. If desired, the coating may comprise pores or channels or to facilitate release of active ingredient. Pores and channels may be generated by well known methods, including the addition of organic or inorganic material that is dissolved, extracted or leached from the coating in the environment of use. Certain such pore-forming materials include hydrophilic polymers, such as hydroxyalkylcelluloses (e.g., hydroxypropylmethylcellulose), cellulose ethers, synthetic water-soluble polymers (e.g., polyvinylpyrrolidone, cross-linked polyvinylpyrrolidone and polyethylene oxide), water-soluble polydextrose, saccharides and polysaccharides and alkali metal salts. Alternatively, or in addition, a controlled release coating may include one or more orifices, which may be formed my methods such as those described in U.S. Pat. Nos. 3,845,770; 4,034,758; 4,077,407; 4,088,864; 4,783,337 and 5,071,607. Controlled-release may also be achieved through the use of transdermal patches, using conventional technology (see, e.g., U.S. Pat. No. 4,668,232).

Further examples of controlled release formulations, and components thereof, may be found, for example, in U.S. Pat. Nos. 5,524,060; 4,572,833; 4,587,117; 4,606,909; 4,610,870; 4,684,516; 4,777,049; 4,994,276; 4,996,058; 5,128,143; 5,202,128; 5,376,384; 5,384,133; 5,445,829; 5,510,119; 5,618,560; 5,643,604; 5,891,474; 5,958,456; 6,039,980; 6,143,353; 6,126,969; 6,156,342; 6,197,347; 6,387,394; 6,399,096; 6,437,000; 6,447,796; 6,475,493; 6,491,950; 6,524,615; 6,838,094; 6,905,709; 6,923,984; 6,923,988; and 6,911,217; each of which is hereby incorporated by reference for its teaching of the preparation of controlled release dosage forms.

In addition to or together with the above modes of administration, a compound provided herein may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Compounds are generally administered in a therapeutically effective amount. Preferred systemic doses are no higher than 50 mg per kilogram of body weight per day (e.g., ranging from about 0.001 mg to about 50 mg per kilogram of body weight per day), with oral doses generally being about 5-20 fold higher than intravenous doses (e.g., ranging from 0.01 to 40 mg per kilogram of body weight per day).

The amount of active ingredient that may be combined with the carrier materials to produce a single dosage unit will vary depending, for example, upon the patient being treated, the particular mode of administration and any other co-administered drugs. Dosage units generally contain between from about 10 μg to about 500 mg of active ingredient. Optimal dosages may be established using routine testing, and procedures that are well known in the art.

Pharmaceutical compositions may be packaged for treating conditions responsive to VR1 modulation (e.g., treatment of exposure to vanilloid ligand or other irritant, pain, itch, obesity or urinary incontinence). Packaged pharmaceutical compositions generally include (i) a container holding a pharmaceutical composition that comprises at least one VR1 modulator as described herein and (ii) instructions (e.g., labeling or a package insert) indicating that the contained composition is to be used for treating a condition responsive to VR1 modulation in the patient.

Methods of Use

VR1 modulators provided herein may be used to alter activity and/or activation of capsaicin receptors in a variety of contexts, both in vitro and in vivo. Within certain aspects, VR1 antagonists may be used to inhibit the binding of vanilloid ligand agonist (such as capsaicin and/or RTX) to capsaicin receptor in vitro or in vivo. In general, such methods comprise the step of contacting a capsaicin receptor with one or more VR1 modulators provided herein, in the presence of vanilloid ligand in aqueous solution and under conditions otherwise suitable for binding of the ligand to capsaicin receptor. The VR1 modulator(s) are generally present at a concentration that is sufficient to alter the binding of vanilloid ligand to VR1 in vitro (using the assay provided in Example 5) and/or VR1-mediated signal transduction (using an assay provided in Example 6). The capsaicin receptor may be present in solution or suspension (e.g., in an isolated membrane or cell preparation), or in a cultured or isolated cell. Within certain embodiments, the capsaicin receptor is expressed by a neuronal cell present in a patient, and the aqueous solution is a body fluid. Preferably, one or more VR1 modulators are administered to an animal in an amount such that the VR1 modulator is present in at least one body fluid of the animal at a therapeutically effective concentration that is 1 micromolar or less; preferably 500 nanomolar or less; more preferably 100 nanomolar or less, 50 nanomolar or less, 20 nanomolar or less, or 10 nanomolar or less. For example, such compounds may be administered at a therapeutically effective dose that is less than 20 mg/kg body weight, preferably less than 5 mg/kg and, in some instances, less than 1 mg/kg.

Also provided herein are methods for modulating, preferably reducing, the signal-transducing activity (i.e., the calcium conductance) of a cellular capsaicin receptor. Such modulation may be achieved by contacting a capsaicin receptor (either in vitro or in vivo) with one or more VR1 modulators provided herein under conditions suitable for binding of the modulator(s) to the receptor. The VR1 modulator(s) are generally present at a concentration that is sufficient to alter the binding of vanilloid ligand to VR1 in vitro and/or VR1-mediated signal transduction as described herein. The receptor may be present in solution or suspension, in a cultured or isolated cell preparation or in a cell within a patient. For example, the cell may be a neuronal cell that is contacted in vivo in an animal. Alternatively, the cell may be an epithelial cell, such as a urinary bladder epithelial cell (urothelial cell) or an airway epithelial cell that is contacted in vivo in an animal. Modulation of signal tranducing activity may be assessed by detecting an effect on calcium ion conductance (also referred to as calcium mobilization or flux). Modulation of signal transducing activity may alternatively be assessed by detecting an alteration of a symptom (e.g., pain, burning sensation, broncho-constriction, inflammation, cough, hiccup, itch, menopause symptoms, urinary incontinence or overactive bladder) of a patient being treated with one or more VR1 modulators provided herein.

VR1 modulator(s) provided herein are preferably administered to a patient (e.g., a human) orally or topically, and are present within at least one body fluid of the animal while modulating VR1 signal-transducing activity. Preferred VR1 modulators for use in such methods modulate VR1 signal-transducing activity in vitro at a concentration of 1 nanomolar or less, preferably 100 picomolar or less, more preferably 20 picomolar or less, and in vivo at a concentration of 1 micromolar or less, 500 nanomolar or less, or 100 nanomolar or less in a body fluid such as blood.

The present invention further provides methods for treating conditions responsive to VR1 modulation. Within the context of the present invention, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to VR1 modulation" if it is characterized by inappropriate activity of a capsaicin receptor, regardless of the amount of vanilloid ligand present locally, and/or if modulation of capsaicin receptor activity results in alleviation of the condition or a symptom thereof. Such conditions include, for example, symptoms resulting from exposure to VR1-activating stimuli, pain, respiratory disorders (such as cough, asthma, chronic obstructive pulmonary disease, chronic bronchitis, cystic fibrosis and rhinitis, including allergic rhinitis, such as seasonal an perennial rhinitis, and non-allergic rhinitis), depression, itch, menopause symptoms, urinary incontinence, overactive bladder, acoustic injury (e.g., of the cochlea), tinnitus, hyperacusis, diabetes and prediabetic conditions (e.g., insulin resistance or glucose tolerance), hiccup and obesity, as described in more detail below. Such conditions may be diagnosed and monitored using criteria that have been established in the art. Patients may include humans, domesticated companion animals and livestock, with dosages as described above.

Treatment regimens may vary depending on the compound used and the particular condition to be treated; however, for treatment of most disorders, a frequency of administration of 4 times daily or less is preferred. In general, a dosage regimen of 2 times daily is more preferred, with once a day dosing particularly preferred. For the treatment of acute pain, a single dose that rapidly reaches effective concentrations is desirable. It will be understood, however, that the specific dose level and treatment regimen for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dose sufficient to provide effective therapy is preferred. Patients may generally be monitored for therapeutic effectiveness using medical or veterinary criteria suitable for the condition being treated or prevented.

Patients experiencing symptoms resulting from exposure to capsaicin receptor-activating stimuli include individuals with burns caused by heat, light, tear gas or acid and those whose mucous membranes are exposed (e.g., via ingestion, inhalation or eye contact) to capsaicin (e.g., from hot peppers or in pepper spray) or a related irritant such as acid, tear gas, infectious agent(s) or air pollutant(s). The resulting symptoms (which may be treated using VR1 modulators, especially antagonists, provided herein) may include, for example, pain, broncho-constriction and inflammation.

Pain that may be treated using the VR1 modulators provided herein may be chronic or acute and includes, but is not limited to, peripheral nerve-mediated pain (especially neuropathic pain). Compounds provided herein may be used in the treatment of, for example, postmastectomy pain syndrome, stump pain, phantom limb pain, oral neuropathic pain, toothache (dental pain), denture pain, postherpetic neuralgia, diabetic neuropathy, chemotherapy-induced neuropathy, reflex sympathetic dystrophy, trigeminal neuralgia, osteoarthritis, rheumatoid arthritis, fibromyalgia, Guillain-Barre syndrome, meralgia paresthetica, burning-mouth syndrome and/or pain associated with nerve and root damage, including as pain associated with peripheral nerve disorders (e.g., nerve entrapment and brachial plexus avulsions, amputation, peripheral neuropathies including bilateral peripheral neuropathy, tic douloureux, atypical facial pain, nerve root damage, and arachnoiditis). Additional neuropathic pain conditions include causalgia (reflex sympathetic dystrophy—RSD, secondary to injury of a peripheral nerve), neuritis (including, for example, sciatic neuritis, peripheral neuritis, polyneuritis, optic neuritis, postfebrile neuritis, migrating neuritis, segmental neuritis and Gombault's neuritis), neuronitis, neuralgias (e.g., those mentioned above, cervicobrachial neuralgia, cranial neuralgia, geniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia, splenopalatine neuralgia, supraorbital neuralgia and vidian neuralgia), surgery-related pain, musculoskeletal pain, myofascial pain syndromes, AIDS-related neuropathy, MS-related neuropathy, central nervous system pain (e.g., pain due to brain stem damage, sciatica, and ankylosing spondylitis), and spinal pain, including spinal cord injury-related pain. Headache, including headaches involving peripheral nerve activity may also be treated as described herein. Such pain includes, for example, such as sinus, cluster (i.e., migranous neuralgia) and tension headaches, migraine, temporomandibular pain and maxillary sinus pain. For example, migraine headaches may be prevented by administration of a compound provided herein as soon as a pre-migrainous aura is experienced by the patient. Further conditions that can be treated as described herein include Charcot's pains, intestinal gas pains, ear pain, heart pain, muscle pain, eye pain, orofacial pain (e.g., odontalgia), abdominal pain, gynaecological pain (e.g., menstrual pain, dysmenorrhoea, pain associated with cystitis, labor pain, chronic pelvic pain, chronic prostitis and endometriosis), acute and chronic back pain (e.g., lower back pain), gout, scar pain, hemorrhoidal pain, dyspeptic pains, angina, nerve root pain, "non-painful" neuropathies, complex regional pain syndrome, homotopic pain and heterotopic pain—including pain associated with carcinoma, often referred to as cancer pain (e.g., in patients with bone cancer), pain (and inflammation) associated with venom exposure (e.g., due to snake bite, spider bite, or insect sting) and trauma associated pain (e.g., post-surgical pain, episiotomy pain, pain from cuts, musculoskeletal pain, bruises and broken bones, and burn pain, especially primary hyperalgesia associated therewith). Additional pain conditions that may be treated as described herein include pain associated with respiratory disorders as described above, autoimmune diseases, immunodeficiency disorders, hot flashes, inflammatory bowel disease, gastroesophageal reflux disease (GERD), irritable bowel syndrome and/or inflammatory bowel disease.

Within certain aspects, VR1 modulators provided herein may be used for the treatment of mechanical pain. As used herein, the term "mechanical pain" refers to pain other than headache pain that is not neuropathic or a result of exposure to heat, cold or external chemical stimuli. Mechanical pain includes physical trauma (other than thermal or chemical burns or other irritating and/or painful exposures to noxious chemicals) such as post-surgical pain and pain from cuts, bruises and broken bones; toothache; denture pain; nerve root pain; osteoarthritis; rheumatoid arthritis; fibromyalgia; meralgia paresthetica; back pain; cancer-associated pain; angina; carpel tunnel syndrome; and pain resulting from bone fracture, labor, hemorrhoids, intestinal gas, dyspepsia, and menstruation.

Itching conditions that may be treated include psoriatic pruritus, itch due to hemodialysis, aguagenic pruritus, and itching associated with vulvar vestibulitis, contact dermatitis, insect bites and skin allergies. Urinary tract conditions that may be treated as described herein include urinary incontinence (including overflow incontinence, urge incontinence and stress incontinence), as well as overactive or unstable bladder conditions (including bladder detrusor hyper-reflexia, detrusor hyper-reflexia of spinal origin and bladder hypersensitivity). In certain such treatment methods, VR1 modulator is administered via a catheter or similar device, resulting in direct injection of VR1 modulator into the bladder. Compounds provided herein may also be used as anti-tussive agents (to prevent, relieve or suppress coughing, including cough induced by medications such as ACE inhibitors) and for the treatment of hiccup, for the treatment of menopause symptoms such as hot flashes, and to promote weight loss in an obese patient.

Within other aspects, VR1 modulators provided herein may be used within combination therapy for the treatment of conditions involving pain and/or inflammatory components. Such conditions include, for example, autoimmune disorders and pathologic autoimmune responses known to have an inflammatory component including, but not limited to, arthritis (especially rheumatoid arthritis), psoriasis, Crohn's disease, lupus erythematosus, irritable bowel syndrome, tissue graft rejection, and hyperacute rejection of transplanted organs. Other such conditions include trauma (e.g., injury to the head or spinal cord), cardio- and cerebro-vascular disease and certain infectious diseases.

Suitable dosages for VR1 modulator within such combination therapy are generally as described above. Dosages and methods of administration of anti-inflammatory agents can be found, for example, in the manufacturer's instructions in the *Physician's Desk Reference*. In certain embodiments, the combination administration of a VR1 modulator with an anti-inflammatory agent results in a reduction of the dosage of the anti-inflammatory agent required to produce a therapeutic effect (i.e., a decrease in the minimum therapeutically effective amount). Thus, preferably, the dosage of anti-inflammatory agent in a combination or combination treatment method is less than the maximum dose advised by the manufacturer for administration of the anti-inflammatory agent without combination administration of a VR1 antagonist. More preferably this dosage is less than ¾, even more preferably less than ½, and highly preferably, less than ¼ of the maximum dose, while most preferably the dose is less than 10% of the maximum dose advised by the manufacturer for administration of the anti-inflammatory agent(s) when administered without combination administration of a VR1 antagonist. It will be apparent that the dosage amount of VR1 antagonist component of the combination needed to achieve the desired effect may similarly be affected by the dosage amount and potency of the anti-inflammatory agent component of the combination.

In certain preferred embodiments, the combination administration of a VR1 modulator with an anti-inflammatory agent is accomplished by packaging one or more VR1 modulators and one or more anti-inflammatory agents in the same package, either in separate containers within the package or in the same contained as a mixture of one or more VR1 antagonists and one or more anti-inflammatory agents. Preferred mixtures are formulated for oral administration (e.g., as pills, capsules, tablets or the like). In certain embodiments, the package comprises a label bearing indicia indicating that the one or more VR1 modulators and one or more anti-inflammatory agents are to be taken together for the treatment of an inflammatory pain condition.

Within further aspects, VR1 modulators provided herein may be used in combination with one or more additional pain relief medications. Certain such medications are also anti-inflammatory agents, and are listed above. Other such medications are analgesic agents, including narcotic agents which typically act at one or more opioid receptor subtypes (e.g., μ, κ and/or δ), preferably as agonists or partial agonists. Such agents include opiates, opiate derivatives and opioids, as well as pharmaceutically acceptable salts and hydrates thereof. Specific examples of narcotic analgesics include, within preferred embodiments, alfentanil, alphaprodine, anileridine, bezitramide, buprenorphine, butorphanol, codeine, diacetyldihydromorphine, diacetylmorphine, dihydrocodeine, diphenoxylate, ethylmorphine, fentanyl, heroin, hydrocodone, hydromorphone, isomethadone, levomethorphan, levorphane, levorphanol, meperidine, metazocine, methadone, methorphan, metopon, morphine, nalbuphine, opium extracts, opium fluid extracts, powdered opium, granulated opium, raw opium, tincture of opium, oxycodone, oxymorphone, paregoric, pentazocine, pethidine, phenazocine, piminodine, propoxyphene, racemethorphan, racemorphan, sulfentanyl, thebaine and pharmaceutically acceptable salts and hydrates of the foregoing agents.

Other examples of narcotic analgesic agents include acetorphine, acetyldihydrocodeine, acetylmethadol, allylprodine, alphracetylmethadol, alphameprodine, alphamethadol, benzethidine, benzylmorphine, betacetylmethadol, betameprodine, betamethadol, betaprodine, clonitazene, codeine methylbromide, codeine-N-oxide, cyprenorphine, desomorphine, dextromoramide, diampromide, diethylthiambutene, dihydromorphine, dimenoxadol, dimepheptanol, dimethylthiamubutene, dioxaphetyl butyrate, dipipanone, drotebanol, ethanol, ethylmethylthiambutene, etonitazene, etorphine, etoxeridine, furethidine, hydromorphinol, hydroxypethidine, ketobemidone, levomoramide, levophenacylmorphan, methyldesorphine, methyldihydromorphine, morpheridine, morphine methylpromide, morphine methylsulfonate, morphine-N-oxide, myrophin, naloxone, naltyhexone, nicocodeine, nicomorphine, noracymethadol, norlevorphanol, normethadone, normorphine, norpipanone, pentazocaine, phenadoxone, phenampromide, phenomorphan, phenoperidine, piritramide, pholcodine, proheptazoine, properidine, propiran, racemoramide, thebacon, trimeperidine and the pharmaceutically acceptable salts and hydrates thereof.

Further specific representative analgesic agents include, for example acetaminophen (paracetamol); ibuprofen; aspirin and other NSAIDs described above; NR2B antagonists; bradykinin antagonists; anti-migraine agents; anticonvulsants such as oxcarbazepine and carbamazepine; antidepressants (such as TCAs, SSRIs, SNRIs, substance P antagonists, etc.); spinal blocks; pentazocine/naloxone; meperidine; levorphanol; buprenorphine; hydromorphone; fentanyl; sufentanyl; oxycodone; oxycodone/acetaminophen, nalbuphine and oxymorphone. Still further analgesic agents include CB2-receptor agonists, such as AM1241, capsaicin receptor antagonists and compounds that bind to the α2δ subunit of voltage-gated calcium channels, such as gabapentin and pregabalin.

Representative anti-migraine agents for use in combination with a VR1 modulator provided herein include CGRP antagonists, ergotamines and 5-HT$_1$ agonists, such as sumatripan, naratriptan, zolmatriptan and rizatriptan.

Within still further aspects, modulators provided herein may be used, for example, in the treatment of pulmonary disorders such as asthma, in combination with one or more beta(2)-adrenergic receptor agonists or leukotriene receptor antagonists (e.g., agents that inhibits the cysteinyl leukotriene CysLT$_1$ receptor). CysLT$_1$ antagonists include montelukast, zafirlukast, and pranlukast.

For the treatment or prevention of cough, a VR1 modulator as provided herein may be used in combination with other medication designed to treat this condition, such as antibiotics, anti-inflammatory agents, cystinyl leukotrienes, histamine antagonists, corticosteroids, opioids, NMDA antagonists, proton pump inhibitors, nociceptin, neurokinin (NK1, NK2 and NK3) and bradykinin (BK1 and BK2) receptor antagonists, cannabinoids, blockers of Na+-dependent channels and large conductance Ca$^{+2}$-dependent K$^+$-channel activators. Specific agents include dexbrompheniramine plus pseudoephedrine, loratadine, oxymetazoline, ipratropium, albuterol, beclomethasone, morphine, codeine, pholcodeine and dextromethorphan.

The present invention further provides combination therapy for the treatment of urinary incontinence. Within such aspects, a VR1 modulator provided herein may be used in combination with other medication designed to treat this condition, such as estrogen replacement therapy, progesterone congeners, electrical stimulation, calcium channel blockers, antispasmodic agents, cholinergic antagonists, antimuscarinic drugs, tricyclic antidepressants, SNRIs, beta adrenoceptor agonists, phosphodiesterase inhibitors, potassium channel openers, nociceptin/orphanin FQ (OP4) agonists, neurokinin (NK1 and NK2) antagonists, P2X3 antagonists, musculotrophic drugs and sacral neuromodulation. Specific agents include oxybutinin, emepronium, tolterodine, flavoxate, flurbiprofen, tolterodine, dicyclomine, propiverine, propantheline, dicyclomine, imipramine, doxepin, duloxetine, 1-deamino-8-D-arginine vasopressin, muscarinic receptor antagonists such as tolterodine and anticholinergic agents such as oxybutynin.

Suitable dosages for VR1 modulator within such combination therapy are generally as described above. Dosages and methods of administration of other pain relief medications can be found, for example, in the manufacturer's instructions in the *Physician's Desk Reference*. In certain embodiments, the combination administration of a VR1 modulator with one or more additional pain medications results in a reduction of the dosage of each therapeutic agent required to produce a therapeutic effect (e.g., the dosage or one or both agent may less than ¾, less than ½, less than ¼ or less than 10% of the maximum dose listed above or advised by the manufacturer).

For use in combination therapy, pharmaceutical compositions as described above may further comprise one or more additional medications as described above. In certain such compositions, the additional medication is an analgesic. Also provided herein are packaged pharmaceutical preparations comprising one or more VR1 modulators and one or more additional medications (e.g., analgesics) in the same package. Such packaged pharmaceutical preparations generally include (i) a container holding a pharmaceutical composition that comprises at least one VR1 modulator as described herein; (ii) a container holding a pharmaceutical composition that comprises at least one additional medication (such as a pain relief and/or anti-inflammatory medication) as described above and (iii) instructions (e.g., labeling or a package insert) indicating that the compositions are to be used simultaneously, separately or sequentially for treating or preventing a condition responsive to VR1 modulation in the patient (such as a condition in which pain and/or inflammation predominates).

Compounds that are VR1 agonists may further be used, for example, in crowd control (as a substitute for tear gas) or personal protection (e.g., in a spray formulation) or as pharmaceutical agents for the treatment of pain, itch, menopause symptoms, urinary incontinence or overactive bladder via capsaicin receptor desensitization. In general, compounds for use in crowd control or personal protection are formulated and used according to conventional tear gas or pepper spray technology.

Within separate aspects, the present invention provides a variety of non-pharmaceutical in vitro and in vivo uses for the compounds provided herein. For example, such compounds may be labeled and used as probes for the detection and localization of capsaicin receptor (in samples such as cell preparations or tissue sections, preparations or fractions thereof). In addition, compounds provided herein that comprise a suitable reactive group (such as an aryl carbonyl, nitro or azide group) may be used in photoaffinity labeling studies of receptor binding sites. In addition, compounds provided herein may be used as positive controls in assays for receptor activity, as standards for determining the ability of a candidate agent to bind to capsaicin receptor, or as radiotracers for positron emission tomography (PET) imaging or for single photon emission computerized tomography (SPECT). Such methods can be used to characterize capsaicin receptors in living subjects. For example, a VR1 modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of capsaicin receptor in the sample. Detection assays, including receptor autoradiography (receptor mapping) of capsaicin receptor in cultured cells or tissue samples may be performed as described by Kuhar in sections 8.1.1 to 8.1.9 of Current Protocols in Pharmacology (1998) John Wiley & Sons, New York.

Compounds provided herein may also be used within a variety of well known cell separation methods. For example, modulators may be linked to the interior surface of a tissue culture plate or other support, for use as affinity ligands for immobilizing and thereby isolating, capsaicin receptors (e.g., isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

VR1 modulators provided herein may further be used within assays for the identification of other agents that bind to capsaicin receptor. In general, such assays are standard competition binding assays, in which bound, labeled VR1 modulator is displaced by a test compound. Briefly, such assays are performed by: (a) contacting capsaicin receptor with a radiolabeled VR1 modulator as described herein, under conditions that permit binding of the VR1 modulator to capsaicin receptor, thereby generating bound, labeled VR1 modulator; (b) detecting a signal that corresponds to the amount of bound, labeled VR1 modulator in the absence of test agent; (c) contacting the bound, labeled VR1 modulator with a test agent; (d) detecting a signal that corresponds to the amount of bound labeled VR1 modulator in the presence of test agent; and (e) detecting a decrease in signal detected in step (d), as compared to the signal detected in step (b).

The following Examples are offered by way of illustration and not by way of limitation. Unless otherwise specified all reagents and solvent are of standard commercial grade and are used without further purification. Using routine modifications, the starting materials may be varied and additional steps employed to produce other compounds provided herein.

EXAMPLES

Mass Spectroscopy data provide in the following examples is Electrospray MS, obtained in positive ion mode with a 15V or 30V cone voltage, using a Micromass Time-of-Flight LCT, equipped with a Waters 600 pump, Waters 996 photodiode array detector, Gilson 215 autosampler, and a Gilson 841 microinjector. MassLynx (Advanced Chemistry Development, Inc; Toronto, Canada) version 4.0 software is used for data collection and analysis. Sample volume of 1 microliter is injected onto a 50×4.6 mm Chromolith SpeedROD C18 column, and eluted using a 2-phase linear gradient at 6 ml/min flow rate. Sample is detected using total absorbance count over the 220-340 nm UV range. The elution conditions are: Mobile Phase A-95/5/0.05 Water/Methanol/TFA; Mobile Phase B-5/95/0.025 Water/Methanol/TFA.

| Gradient: | |
|---|---|
| Time (min) | % B |
| 0 | 10 |
| 0.5 | 100 |
| 1.2 | 100 |
| 1.21 | 10 |

The total run time is 2 minutes inject to inject.

Example 1

Preparation of Representative Intermediates

This Example illustrates the preparation of representative intermediates useful in the synthesis of 2-phenoxy pyrimidinone derivatives.

A. Ethyl 3-nitriloalaninate

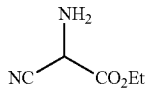

A mixture of ethyl cyanoglyoxylate-2-oxime (50 g, 352 mmol) in 440 mL of water is cautiously treated with 340 mL of saturated aqueous $NaHCO_3$, followed by portionwise addition of sodium hydrosulfite (165 g, 950 mmol). The reaction is then heated to an internal temperature of 35° C. for 35 min. After cooling to RT, the reaction is saturated with NaCl (approx. 250 g) and extracted with $CH_2Cl_2$ (6×150 mL). The combined $CH_2Cl_2$ extracts are dried ($Na_2SO_4$), filtered, and concentrated in vacuo to give the title compound as a brown oil. $^1$H NMR (400 MHz, $CDCl_3$) δ 4.43 (1H, s), 4.34 (2H, q, J 7.2), 2.30 (2H, bs), 1.35 (3H, t, J 7.2).

B. Ethyl 5-amino-1-methyl-1H-imidazole-4-carboxylate

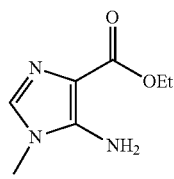

A mixture of ethyl 3-nitriloalaninate (26.7 g, 208 mmol) and triethyl orthoformate (34.6 mL, 208 mmol) in 340 mL of acetonitrile is heated to 90° C. and stirred for 70 min. After cooling to RT, methylamine (25.9 mL of a 33 wt % solution in EtOH, 208 mmol) is added, followed by 20 h of stirring at RT. The reaction mixture is then concentrated in vacuo and dissolved in approx. 200 mL of 1N HCl. The aqueous solution is washed with $CH_2Cl_2$ (3×100 mL), basified to pH=9-10 with solid $NaHCO_3$, and extracted with $CH_2Cl_2$ (5×100 mL). The combined $CH_2Cl_2$ extracts are dried ($Na_2SO_4$), filtered, and concentrated to give a brown solid. The solid is slurried in EtOAc, filtered, and washed with $Et_2O$ to give the title compound as an off-white solid. $^1$H NMR (400 MHz, $CDCl_3$) δ 7.03 (1H, s), 4.88 (2H, bs), 4.33 (2H, q, J 7.2), 3.45 (3H, s), 1.37 (3H, t, J 7.2).

C. 1-(4-Fluorophenyl)-9-methyl-2-thioxo-1,2,3,9-tetrahydro-6H-purin-6-one hydrochloride

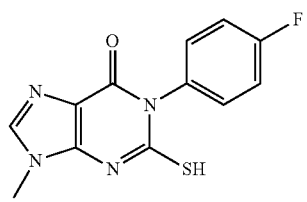 [SMILES: Cn1cnc2c(=O)n(-c3ccc(F)cc3)c(S)nc21]

Ethyl 5-amino-1-methyl-1H-imidazole-4-carboxylate (8.45 g, 0.05 moles) and 4-fluorophenyl isothiocyanate (7.65 g, 0.05 moles) are stirred in pyridine (125 mL) at 45° C. for 20 h. The reaction mixture is concentrated under vacuum and diluted by the addition of ice cold water. The reaction mixture is extracted with $CH_2Cl_2$ (2×250 mL), washed with water (200 mL) and dried over $MgSO_4$. The filtrate is evaporated in vacuo to give crude intermediate as red orange viscous oil. The oil is slurried in 1% aqueous sodium hydroxide solution (300 mL) and heated at 90° C. for 20 h. The reaction mixture is cooled and the solid is filtered. The filtrate is evaporated in vacuo to reduced volume (100 mL). The mixture is acidified using concentrated HCl to pH 4.0 and allowed stand at RT overnight. The yellow solid which separates is filtered and dried at 70° C., to afford the title compound. $^1$H NMR (400 MHz, DMSO-$d_6$) δ 7.8 (1H, s), 7.2-7.4 (4H, m), 3.74 (3H, s).

D. 2-Chloro-1-(4-fluorophenyl)-9-ethyl-1,9-dihydro-6H-purin-6-one

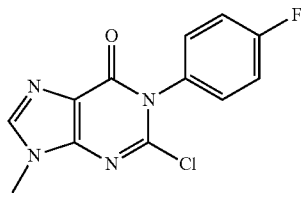 [SMILES: Cn1cnc2c(=O)n(-c3ccc(F)cc3)c(Cl)nc21]

1-(4-Fluorophenyl)-9-methyl-2-thioxo-1,2,3,9-tetrahydro-6H-purin-6-one hydrochloride (6.5 g, 0.021 mol) is suspended in a large excess of phosphorous oxychloride (150 mL) and heated to 135° C. for 40 h. The reaction mixture is cooled, evaporated in vacuo, and azeotroped twice with toluene. The resulting sticky brown oil is dissolved in DCM (200 mL) then neutralized with saturated $NaHCO_3$ (aqueous). The aqueous layer is extracted with DCM (2×200 mL) and dried ($MgSO_4$). The dried extract is filtered and concentrated under vacuum to afford crude product as a light brown solid. The crude product is purified by flash column chromatography using 1-2.5% $MeOH/CH_2Cl_2$ to afford the title compound as white solid. $^1$H NMR (400 MHz, $CDCl_3$) δ 7.75 (1H, s), 7.2-7.35 (4H, m), 3.85 (3H, s).

E. Ethyl 3-aminopyridine-2-carboxylate

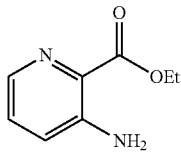

A mixture of 3-aminopyridine-2-carboxylic acid (6.4 g, 46.3 mmol) in 26 mL of EtOH and 8 mL of concentrated sulfuric acid is heated to reflux for 2 days. After cooling, the mixture is concentrated to about 15-20 mL and poured into 20 g of ice. The mixture is basified to pH 8-9 with concentrated $NH_4OH$ while cooling in an ice bath. The resulting brown precipitate is filtered off, and the filtrate is extracted with ether (4×60 mL). The combined ether extracts are washed with brine (4×60 mL), dried ($Na_2SO_4$), filtered, and evaporated to give a yellow/brown solid. This solid is combined with that from the above filtration and the whole is triturated with cold ether to give the title compound as a light brown solid. $^1$H NMR (400 MHz, $CDCl_3$) δ 8.08 (1H, m), 7.21 (1H, m), 7.03 (1H, m), 5.74 (2H, bs), 4.44 (2H, q, J 7.2, 6.9), 1.45 (3H, t, J 6.9).

F. 3-(4-Fluorophenyl)-2-thioxo-2,3-dihydropyrido[3,2-d]pyrimidin-4(1H)-one

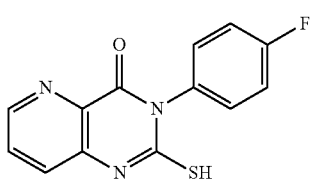 [SMILES: O=c1c2ncccc2nc(S)n1-c1ccc(F)cc1]

A mixture of ethyl 3-aminopyridine-2-carboxylate (2.0 g, 12.0 mmol) and 4-fluorophenylisothiocyanate (1.84 g, 12.0 mmol) in 7 mL of anhydrous pyridine is stirred at 45° C. for 21 h. After cooling, the pyridine is evaporated in vacuo, and ice water is added to the residue. The resulting mixture is slurried in EtOAc and filtered to give the title compound as a white solid. $^1$H NMR (400 MHz, DMSO-$d_6$) δ 8.59 (1H, m), 7.79 (2H, m), 7.33 (4H, m).

G. 2-Chloro-3-(4-fluorophenyl)pyrido[3,2-d]pyrimidin-4(3H)-one

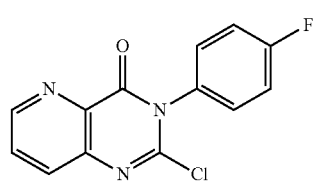 [SMILES: O=c1c2ncccc2nc(Cl)n1-c1ccc(F)cc1]

A mixture of 3-(4-fluorophenyl)-2-thioxo-2,3-dihydropyrido[3,2-d]pyrimidin-4(1H)-one (2.6 g, 9.5 mmol) in 30 mL of $POCl_3$ is heated to 135° C. and stirred for 2 days. After cooling to RT, the excess $POCl_3$ is removed in vacuo, and the residue is azeotroped twice with toluene. The resulting sticky brown oil/solid mix is dissolved in $CH_2Cl_2$ and neutralized to pH 7-8 with saturated $NaHCO_3$. The layers are separated, and the $CH_2Cl_2$ layer is dried ($Na_2SO_4$), filtered, and evaporated to give a brown sticky solid. Purification by column chromatography (gradient from $CH_2Cl_2$ to 20% EtOAc/$CH_2Cl_2$) affords the title compound as an off-white solid. $^1$H NMR (400 MHz, $CDCl_3$) δ 8.91 (1H, m), 8.05 (1H, m), 7.74 (1H, m), 7.28 (4H, m).

H. Acetic Formic Anhydride

Acetic anhydride (35.94 g, 352 mmol) and formic acid (16.20 g, 352 mmol) are added to a round bottomed flask, and heated at 55° C. for 3 h. The reaction mixture is used in Example 1I without further purification.

I. Ethyl N-formyl-3-nitriloalaninate

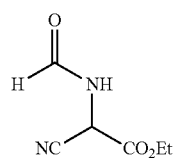

Ethyl 3-nitriloalaninate (26.9 g, 210 mmol) is dissolved in anhydrous ether (200 mL), and cooled in an ice/water bath. Acetic formic anhydride (prepared as a mixture as described above) is added dropwise. When the addition is finished, the reaction mixture is allowed to warm to RT and stirred at RT overnight. Most volatiles are removed in vacuo, and the residue solvents are removed by co-evaporation with toluene (100 mL×4). The red oil obtained precipitates upon scratching in ether, and the resulting solids are recrystallized in ether to give the title compound as a white solid. $^1$H NMR (400 MHz, $CDCl_3$) 8.32 (1H, s), 7.26 (1H, s), 6.46 (1H, bs,), 5.56 (1H, d, J 7.8), 4.39 (2H, q), 1.37 (3H, t).

J. Ethyl 5-amino-1,3-thiazole-4-carboxylate

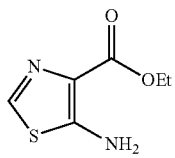

Ethyl N-formyl-3-nitriloalaninate (11.22 g, 71.86 mmol) is dissolved in anhydrous benzene (220 mL). Following the addition of Lawesson's reagent (14.53 g, 35.93 mmol), the suspension is refluxed for 24 h. Most of the solvent is removed in vacuo, and the viscous red residue is absorbed on silica gel and loaded to a silica gel column (elution solvent: EtOAc:hexanes=50:50). The title compound is obtained as yellow solids. $^1$H NMR (400 MHz, CDCl$_3$) 7.87 (1H, s), 7.26 (1 H, s), 6.01 (2H, broad s), 4.38 (2H, q), 1.41 (3H, t).

K. 6-(4-Fluorophenyl)-5-mercapto[1,3]thiazolo[5,4-d]pyrimidin-7(6H)-one hydrochloride

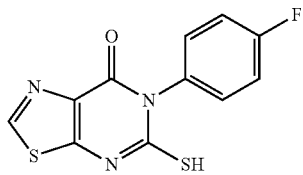 [SMILES: O=c1c2ncsc2nc(S)n1-c1ccc(F)cc1]

Ethyl 5-amino-1,3-thiazole-4-carboxylate (1.05 g, 6.10 mmol) and 4-fluorophenyl isothiocyanate (0.93 g, 6.10 mmol) are added to pyridine (3.5 mL) and heated at 45° C. for 15 h. Most of the solvent is removed under vacuum, and the resulting yellow solids are dissolved in CH$_2$Cl$_2$ (150 mL) and washed with H$_2$O (20 mL×2) and brine (20 mL×2). The CH$_2$Cl$_2$ phase is dried over MgSO$_4$, and the solvent is removed under reduced pressure. The resulting residue is treated with 1% NaOH solution (37 mL) and heated at 90° C. for 15 h. The reaction mixture is filtered and the filtrate adjusted to pH 3 by the addition of concentrated HCl. Most of the water is removed under vacuum and the yellow solid which separates is filtered and dried to give the title compound as a yellow solid. $^1$H NMR (400 MHz, DMSO-d$_6$) 8.90 (1H, s), 7.31 (4H, m).

L. 5-Chloro-6-(4-fluorophenyl)[1,3]thiazolo[5,4-d]pyrimidin-7(6H)-one

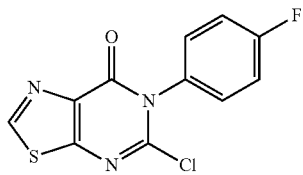 [SMILES: O=c1c2ncsc2nc(Cl)n1-c1ccc(F)cc1]

6-(4-Fluorophenyl)-5-mercapto[1,3]thiazolo[5,4-d]pyrimidin-7(6H)-one hydrochloride (0.2 g, 0.633 mmol) is added to POCl$_3$ (10 mL), and the resulting solution is refluxed at 135° C. for 41 h. Most of the volatiles are removed under reduced pressure and the residual solvent is co-evaporated with toluene (50 mL×3). The dark solid obtained is dissolved in CH$_2$Cl$_2$ (200 mL) and washed with saturated NaHCO$_3$ solution (100 mL×5), brine (50 mL×2), and dried over MgSO$_4$. After removing solvent, silica gel column chromatography (EtOAc:hexanes=50:50) yields the title compound as a yellow solid. $^1$H NMR (400 MHz, CDCl$_3$) 8.88 (1H, s), 7.26 (4H, m).

M. 1-(4-Bromophenyl)-2-mercapto-9-methyl-1,9-dihydro-6H-purin-6-one hydrochloride

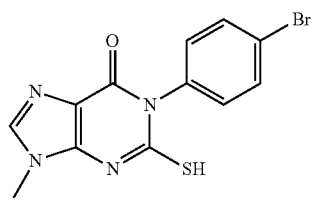 [SMILES: Cn1cnc2c(=O)n(-c3ccc(Br)cc3)c(S)nc21]

Ethyl 5-amino-1-methyl-1H-imidazole-4-carboxylate (3.50 g, 20.69 mmol) and 4-bromophenyl isothiocyanate (4.43 g, 20.69 mmol) are added to pyridine (12 mL). The solution is heated at 45° C. for 3 h. Most of the solvent is removed under vacuum and the resulting solid is dissolved in CH$_2$Cl$_2$ (300 mL). The CH$_2$Cl$_2$ solution is washed with water (30 mL×2), brine (30 mL×2), dried over MgSO$_4$, and concentrated in vacuo. The resulting yellow solid is treated with 1% NaOH aqueous solution (125 mL) and heated at 90° C. for 18 h. The reaction mixture is filtered and the filtrate adjusted pH to 3 by the addition of concentrated HCl. Most of the water is removed under reduced pressure. The resulting solid is collected by filtration, the solid is azeotroped with toluene (30 mL×3) to give the title compound as a yellow solid. $^1$H NMR (400 MHz, CD$_3$OD) 8.10 (1H, s), 7.65 (2H, d), 7.14 (2H, d), 3.85 (3H, s).

N. 1-(4-Bromophenyl)-2-chloro-9-methyl-1,9-dihydro-6H-purin-6-one

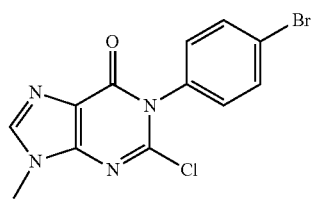 [SMILES: Cn1cnc2c(=O)n(-c3ccc(Br)cc3)c(Cl)nc21]

1-(4-Bromophenyl)-2-mercapto-9-methyl-1,9-dihydro-6H-purin-6-one hydrochloride (2.05 g, 5.49 mmol) is added to POCl$_3$ (87 mL) and the resulting solution is refluxed at 135° C. for 38 h. Most volatiles are removed under vacuum and the residual solvents are co-evaporated with toluene (50 mL×3). The resulting dark solid is dissolved in CH$_2$Cl$_2$ (300 mL), washed with saturated NaHCO$_3$ solution (100 mL×5), brine (50 mL×2), and dried over MgSO$_4$. After removing solvent in vacuo, silica gel column chromatography (EtOAc:hexanes=50:50) gives the title compound as a yellow solid. $^1$H NMR (400 MHz, CDCl$_3$) 7.51 (1H, s), 7.67 (2H, d), 7.14 (2H, d), 3.83 (3H, s); m/z (ES$^+$) 340.90 (M$^+$).

Example 2

Synthesis of Representative 2-Phenoxy Pyrimidinone Derivatives

A. 1-(4-Bromophenyl)-9-methyl-2-(2,3,4-trifluorophenoxy)-1,9-dihydro-6H-purin-6-one (Compound 1)

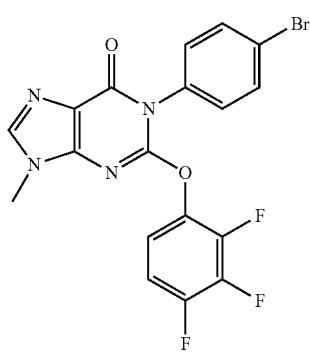 [SMILES: Cn1cnc2c(=O)n(-c3ccc(Br)cc3)c(Oc3ccc(F)c(F)c3F)nc21]

1-(4-Bromophenyl)-2-chloro-9-methyl-1,9-dihydro-6H-purin-6-one (150 mg, 0.4417 mmol) and 2,3,4-trifluorophenol (130.8 mg, 0.8834 mmol) are added to a vial, and the sealed mixture is heated with stirring at 140° C. for 23 h. Silica gel column chromatography (MeOH:CH$_2$Cl$_2$=0.5: 99.5) gives the title compound as a white solid. $^1$H NMR (400 MHz, CDCl$_3$) 7.66 (3H, m), 7.24 (2H, m), 7.00 (2H, m), 3.58 (3H, s). MS (M+1): 451.08; R$_T$=1.31 min. The IC$_{50}$ determined as described in Example 6 is 100 nanomolar or less.

B. 1-(4-Fluorophenyl)-9-methyl-2-(3,4,5-trifluorophenoxy)-1,9-dihydro-6H-purin-6-one (Compound 2)

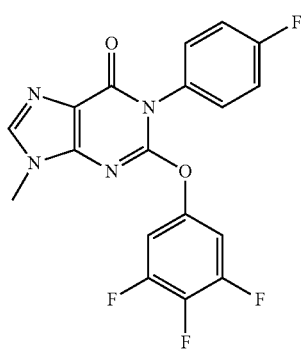 [SMILES: Cn1cnc2c(=O)n(-c3ccc(F)cc3)c(Oc3cc(F)c(F)c(F)c3)nc21]

A mixture of 2-chloro-1-(4-fluorophenyl)-9-ethyl-1,9-dihydro-6H-purin-6-one (55.6 mg, 0.20 mmol) and 3,4,5-trifluorophenol (0.40 mmol) is heated to 140° C. for 36 h. After cooling to RT, the crude mixture is purified by preparative HPLC to give the title compound as a white solid. $^1$H NMR (400 MHz, DMSO-d$_6$) 7.98 (1H, s), 7.55 (2H, m), 7.45 (2H, m), 7.34 (2H, m), 3.53 (3H, S). m/z=391.05 (M+1); R$_T$=0.78 min.

C. 3-(4-Fluorophenyl)-2-[2-fluoro-3-(trifluoromethyl)phenoxy]pyrido[3,2-d]pyrimidin-4(3H)-one (Compound 3)

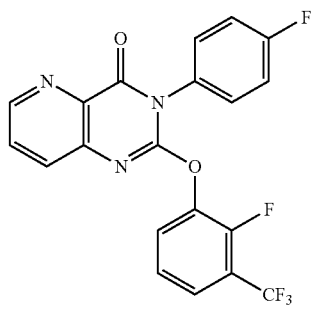

A mixture of 2-chloro-3-(4-fluorophenyl)pyrido[3,2-d]pyrimidin-4(3H)-one (55 mg, 0.20 mmol) and 2-fluoro-3-trifluoromethylphenol (50 µl, 0.40 mmol) is heated to 140° C. for 18 hours. After cooling to RT, the crude mixture is purified by column chromatography (gradient from CH$_2$Cl$_2$ to 20% EtOAc/CH$_2$Cl$_2$) to give the title compound as a white solid. $^1$H NMR (400 MHz, DMSO-d$_6$) 8.71 (1H, m), 7.83 (2H, m), 7.70 (4H, m), 7.45 (3H, m). MS (M+1): 420.07; R$_T$=1.13 min.

D. 5-(2,4-Difluorophenoxy)-6-(4-fluorophenyl)[1,3]thiazolo[5,4-d]pyrimidin-7(6H)-one (Compound 4)

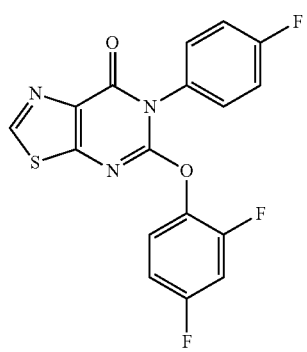 [SMILES: O=c1c2ncsc2nc(Oc2ccc(F)cc2F)n1-c1ccc(F)cc1]

5-Chloro-6-(4-fluorophenyl)[1,3]thiazolo[5,4-d]pyrimidin-7(6H)-one (0.2 mmol) and 2.4-difluorophenol (0.4 mmol) are added to a vial, and the sealed mixture is heated with stirring at 140° C. for 48 h. Silica gel column chromatography (MeOH:CH$_2$Cl$_2$=0.5:99.5) gives the title compound as a slightly yellow solid. $^1$H NMR (400 MHz, CDCl$_3$) 8.70 (1H, s), 7.36 (2H, m), 7.26 (2H, m), 7.14 (1H, m), 6.94 (2H, m). MS (M+1): 376.03; R$_T$=1.33 min.

E. 4-[9-Methyl-6-oxo-2-(2,3,4-trifluorophenoxy)-6,9-dihydro-1H-purin-1-yl]benzonitrile (Compound 5)

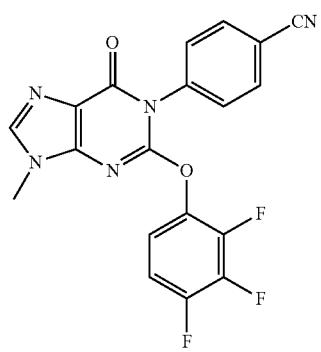 [SMILES: Cn1cnc2c(=O)n(-c3ccc(C#N)cc3)c(Oc3ccc(F)c(F)c3F)nc21]

1-(4-Bromophenyl)-9-methyl-2-(2,3,4-trifluorophenoxy)-1,9-dihydro-6H-purin-6-one (68 mg, 0.1507 mmol), Zn(CN)$_2$ (10.6 mg, 0.0904 mmol), Pd$_2$(dba)$_3$ (4.1 mg, 0.0045 mmol) and 1,1'-bis(diphenylphosphino)ferrocene (5.0 mg, 0.0090 mmol) are added to DMF (1.2 mL) and H$_2$O (0.012 mL). The mixture is purged with N$_2$ for 3 min and then heated at 120° C. for 18 h. The mixture is passed through celite. Water (30 mL) is added and the resulting mixture is extracted with CH$_2$Cl$_2$ (50 mL×4). After drying the CH$_2$Cl$_2$ over MgSO$_4$, the solvent is removed in vacuo. The crude product is purified by column chromatography (MeOH:CH$_2$Cl$_2$=2:98) to afford the title compound as a brown solid. $^1$H NMR (400 MHz, CDCl$_3$) 7.86 (2H, d, J 8), 7.65 (1H, s), 7.53 (2h, d, J 8), 6.95 (2H, m), 3.59 (3H, s). MS (M+1): 398.03; R$_T$=1.22 min.

F. 1-(6-Chloropyridin-3-yl)-9-methyl-2-(3,4,5-trifluorophenoxy)-1H-purin-6(9H)-one (Compound 6)

Step 1. 2-Hydroxy-1-(6-chloropyridin-3-yl)-1,9-dihydro-6H-purin-6-one

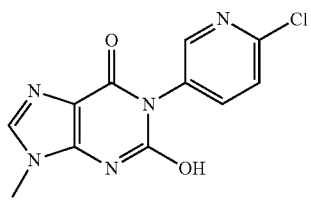 [SMILES: Cn1cnc2c(=O)n(-c3ccc(Cl)nc3)c(O)nc21]

Methyl 5-amino-1-methyl-1H-imidazole-4-carboxylate (1.0 g, 0.006 moles), 2-chloro-5-isocyantopyridine (1.0 g, 0.006 moles) and DMAP (0.4 g, 0.003 mole) are suspended in EtOAc (150 mL) and the resulting reaction mixture is refluxed overnight. The reaction mixture is filtered, washed with EtOAc, and concentrated under vacuum. The white residue is suspended in 1% aqueous NaOH (53 mL) and stirred at 90° C. for 20 h. The reaction mixture is neutralized with 6N HCl and extracted with DCM to afford the title compound.

Step 2. 2-Chloro-1-(6-chloropyridin-3-yl)-1,9-dihydro-6H-purin-6-one

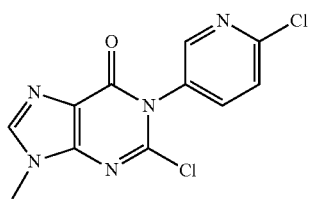 [SMILES: Cn1cnc2c(=O)n(-c3ccc(Cl)nc3)c(Cl)nc21]

2-Hydroxy-1-(6-chloropyridin-3-yl)-1,9-dihydro-6H-purin-6-one from the above reaction is suspended in a large excess of phosphorous oxychloride (150 mL) and heated to 135° C. for 24 h. The reaction mixture is cooled, evaporated in vacuo, and additional toluene is added and evaporated (2×) under reduced pressure. The resulting sticky brown oil is dissolved in DCM (200 mL), and then neutralized with saturated NaHCO$_3$ (aqueous). The aqueous layer is extracted with DCM (2×200 mL) and dried (MgSO$_4$). The dried extract is filtered and concentrated under vacuum to afford crude product as a light brown solid. The crude product is purified by flash column chromatography using 1-2.5% MeOH/CH$_2$Cl$_2$ to afford the title compound as white solid. $^1$H NMR (300 MHz, CDCl$_3$) δ 8.33 (s, 1H), 7.78 (s, 1H), 7.58 (d, J=6 Hz, 1H), 7.53 (d, J=6 Hz, 1H).

Step 3. 1-(6-chloropyridin-3-yl)-9-methyl-2-(3,4,5-trifluorophenoxy)-1H-purin-6(9H)-one (Compound 6)

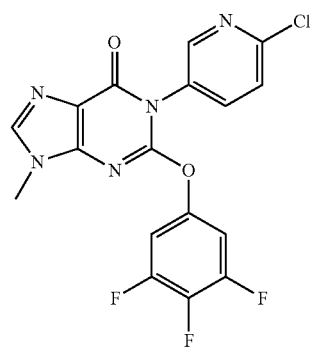 [SMILES: Cn1cnc2c(=O)n(-c3ccc(Cl)nc3)c(Oc3cc(F)c(F)c(F)c3)nc21]

1.0 M KO$^t$Bu in isopropanol (2 mL) is added to the solution of 3,4,5-trifluorophenol (0.29 g, 1.86 mmol) and stirred for 20 minutes at RT. To the resulting phenoxide solution is added a solution of 2-chloro-1-(6-chloropyridin-3-yl)-1,9-dihydro-6H-purin-6-one (0.5 g, 1.69 mmol) in dimethylacetamide (3 mL) and the resulting mixture is stirred overnight at 50° C. The resulting reaction mixture is cooled, quenched with saturated NH$_4$Cl solution, extracted with DCM (2×50 mL) and dried (Na$_2$SO$_4$). The organic layer is filtered and concentrated under vacuum to afford the crude product as a light brown solid. The crude product is further purified by flash column chromatography using 5% MeOH/CH$_2$Cl$_2$ to afford the title compound as white solid. $^1$H NMR (300 MHz, CDCl$_3$) δ 8.41 (s, 1H), 7.55-7.81 (m, 2H), 7.4 (brs, 1H), 6.71-7.02 (m, 2H), 3.85 (s, 3H). MS (M+1): 408.04; R$_T$=1.48 min. The IC$_{50}$ determined as described in Example 6 is 100 nanomolar or less.

G. 5-(9-Methyl-6-oxo-2-(3,4,5-trifluorophenoxy)-6H-purin-1(9H)-yl)picolinonitrile (Compound 7)

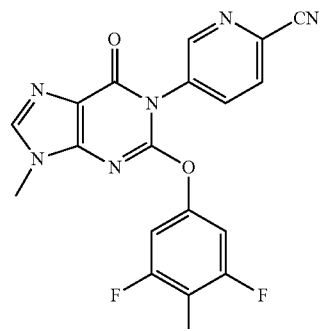

1-(6-chloropyridin-3-yl)-9-methyl-2-(3,4,5-trifluorophenoxy)-1,9-dihydro-6H-purin-6-one (0.3 g, 0.73 mmol), $Zn(CN)_2$ (0.43 mg, 3.65 mmol), $Pd_2(dba)_3$ (0.07 g, 0.073 mmol) and DPPF (0.04 g, 0.073 mmol) are added to DMF (3 mL). The mixture is purged with $N_2$ for 3 min and then heated at 120° C. for 18 h. Water (20 mL) is added and the resulting mixture is extracted with DCM (2×20 mL). The organic layer is passed through celite and $Na_2SO_4$ and the solvent is removed in vacuo. The crude product is purified by column chromatography on silica gel ($MeOH:CH_2Cl_2$=2:98) to afford the title compound as a white solid. $^1$H NMR (300 MHz, $CDCl_3$) δ 8.71 (s, 1H), 7.90 (s, 2H), 7.68 (s, 1H), 7.25 (s, 2H), 6.85-6.89 (m, 2H), 3.65 (s, 3H, s). MS (M+1): 399.07; $R_T$=1.41 min. The $IC_{50}$ determined as described in Example 6 is 100 nanomolar or less.

Example 3

Additional Representative 2-Phenoxy Pyrimidinone Derivatives

Using routine modifications, the starting materials may be varied and additional steps employed to produce other compounds provided herein. Compounds listed in Table I are prepared using such methods. In the column labeled "$IC_{50}$" a * indicates that the $IC_{50}$ determined as described in Example 6 is 100 nanomolar or less (i.e., the concentration of such compounds that is required to provide a 50% decrease in the fluorescence response of cells exposed to one $IC_{50}$ of capsaicin is 100 nanomolar or less). Mass spectroscopy data obtained as described above is presented as M+1 in the column headed "MS", and retention times are provided in the column headed "$R_T$," in minutes.

TABLE I

Representative 2-Phenoxy Pyrimidinone Derivatives

| Compound | Name | MS | $R_T$ | $IC_{50}$ |
|---|---|---|---|---|
| 8 | 1-(4-chlorophenyl)-9-methyl-2-(2,4,6-trifluorophenoxy)-1,9-dihydro-6H-purin-6-one | 406.99 | 1.27 | * |
| 9 | 9-ethyl-1-(4-fluorophenyl)-2-(2,4,6-trifluorophenoxy)-1,9-dihydro-6H-purin-6-one | 405.03 | 1.25 | * |
| 10 | 1-(4-chlorophenyl)-9-methyl-2-(2,3,4-trifluorophenoxy)-1,9-dihydro-6H-purin-6-one | 407.00 | 1.28 | * |

TABLE I-continued

Representative 2-Phenoxy Pyrimidinone Derivatives

| Compound | | Name | MS | $R_T$ | $IC_{50}$ |
|---|---|---|---|---|---|
| 11 | | 9-ethyl-1-(4-fluorophenyl)-2-(2,3,4-trifluorophenoxy)-1,9-dihydro-6H-purin-6-one | 405.04 | 1.26 | * |
| 12 | | 1-(4-fluorophenyl)-9-methyl-2-(2,4,6-trifluorophenoxy)-1,9-dihydro-6H-purin-6-one | 391.03 | 1.23 | * |
| 13 | | 1-(4-fluorophenyl)-9-methyl-2-(2,3,4-trifluorophenoxy)-1,9-dihydro-6H-purin-6-one | 391.04 | 1.24 | * |
| 14 | | 1-(4-chlorophenyl)-2-(2,4-difluorophenoxy)-9-methyl-1,9-dihydro-6H-purin-6-one | 389.02 | 1.25 | * |

TABLE I-continued

Representative 2-Phenoxy Pyrimidinone Derivatives

| Compound | Name | MS | $R_T$ | $IC_{50}$ |
|---|---|---|---|---|
| 15 | 2-(2,4-difluorophenoxy)-9-ethyl-1-(4-fluorophenyl)-1,9-dihydro-6H-purin-6-one | 387.06 | 1.24 | * |
| 16 | 2-(2,4-difluorophenoxy)-1-(4-fluorophenyl)-9-methyl-1,9-dihydro-6H-purin-6-one | 373.03 | 1.22 | * |
| 17 | 2-(2,3-difluorophenoxy)-1-(4-fluorophenyl)-9-methyl-1,9-dihydro-6H-purin-6-one | 373.05 | 1.22 | * |
| 18 | 2-(2,3-difluorophenoxy)-9-ethyl-1-(4-fluorophenyl)-1,9-dihydro-6H-purin-6-one | 387.05 | 1.24 | * |

TABLE I-continued

Representative 2-Phenoxy Pyrimidinone Derivatives

| Compound | | Name | MS | $R_T$ | $IC_{50}$ |
|---|---|---|---|---|---|
| 19 | | 2-(4-chloro-2-fluorophenoxy)-9-ethyl-1-(4-fluorophenyl)-1,9-dihydro-6H-purin-6-one | 403.00 | 1.28 | * |
| 13 | | 2-(4-chloro-2-fluorophenoxy)-1-(4-fluorophenyl)-9-methyl-1,9-dihydro-6H-purin-6-one | 389.00 | 1.26 | * |
| 14 | | 2-(4-chloro-2-fluorophenoxy)-1-(4-chlorophenyl)-9-methyl-1,9-dihydro-6H-purin-6-one | 404.96 | 1.3 | * |
| 15 | | 1-(4-fluorophenyl)-9-methyl-2-(2,4,5-trifluorophenoxy)-1,9-dihydro-6H-purin-6-one | 391.07 | 1.18 | * |

TABLE I-continued

Representative 2-Phenoxy Pyrimidinone Derivatives

| Compound | | Name | MS | $R_T$ | $IC_{50}$ |
|---|---|---|---|---|---|
| 16 | [structure] | 9-ethyl-1-(4-fluorophenyl)-2-(2,4,5-trifluorophenoxy)-1,9-dihydro-6H-purin-6-one | 405.09 | 1.11 | * |
| 17 | [structure] | 1-(4-chlorophenyl)-9-methyl-2-(2,4,5-trifluorophenoxy)-1,9-dihydro-6H-purin-6-one | 407.04 | 1.3 | * |
| 18 | [structure] | 2-(2,3-difluoro-4-methoxyphenoxy)-1-(4-fluorophenyl)-9-methyl-1,9-dihydro-6H-purin-6-one | 403.09 | 0.89 | * |
| 19 | [structure] | 2-(2,3-difluoro-4-methoxyphenoxy)-9-ethyl-1-(4-fluorophenyl)-1,9-dihydro-6H-purin-6-one | 417.11 | 0.56 | * |

TABLE I-continued

Representative 2-Phenoxy Pyrimidinone Derivatives

| Compound | | Name | MS | R$_T$ | IC$_{50}$ |
|---|---|---|---|---|---|
| 20 | | 1-(4-fluorophenyl)-9-methyl-2-(2,3,5-trifluorophenoxy)-1,9-dihydro-6H-purin-6-one | 391.07 | 1.21 | * |
| 21 | | 1-(4-chlorophenyl)-2-(2,3-difluorophenoxy)-9-methyl-1,9-dihydro-6H-purin-6-one | 389.05 | 1.26 | * |
| 22 | | 2-(2-chloro-4-fluorophenoxy)-1-(4-fluorophenyl)-9-methyl-1,9-dihydro-6H-purin-6-one | 389.05 | 1.22 | * |
| 23 | | 2-(2-chloro-4-fluorophenoxy)-1-(4-chlorophenyl)-9-methyl-1,9-dihydro-6H-purin-6-one | 405.02 | 0.6 | * |

TABLE I-continued

Representative 2-Phenoxy Pyrimidinone Derivatives

| Compound | Name | MS | $R_T$ | $IC_{50}$ |
|---|---|---|---|---|
| 24 | 1-(4-fluorophenyl)-9-methyl-2-(2,3,6-trifluorophenoxy)-1,9-dihydro-6H-purin-6-one | 391.07 | 1.18 | * |
| 25 | 1-(4-chlorophenyl)-9-methyl-2-(2,3,6-trifluorophenoxy)-1,9-dihydro-6H-purin-6-one | 407.04 | 0.62 | * |
| 26 | 9-ethyl-1-(4-fluorophenyl)-2-(2,3,5-trifluorophenoxy)-1,9-dihydro-6H-purin-6-one | 405.09 | 0.72 | * |
| 27 | 1-(4-chlorophenyl)-9-methyl-2-(2,3,5-trifluorophenoxy)-1,9-dihydro-6H-purin-6-one | 407.04 | 0.69 | * |
| 28 | 4-{[1-(4-chlorophenyl)-9-methyl-6-oxo-6,9-dihydro-1H-purin-2-yl]oxy}-2,3-difluorobenzonitrile | 414.06 | 1.25 | * |

TABLE I-continued

Representative 2-Phenoxy Pyrimidinone Derivatives

| Compound | | Name | MS | $R_T$ | $IC_{50}$ |
|---|---|---|---|---|---|
| 29 | | 2,3-difluoro-4-{[1-(4-fluorophenyl)-9-methyl-6-oxo-6,9-dihydro-1H-purin-2-yl]oxy}benzonitrile | 398.07 | 1.22 | * |
| 30 | | 1-(4-chlorophenyl)-9-methyl-2-(3,4,5-trifluorophenoxy)-1,9-dihydro-6H-purin-6-one | 407.04 | 1.39 | * |
| 31 | | 2-(2,4-difluorophenoxy)-3-(4-fluorophenyl)pyrido[3,2-d]pyrimidin-4(3H)-one | 370.11 | 1.26 | * |
| 32 | | 3-(4-fluorophenyl)-2-(2,3,4-trifluorophenoxy)pyrido[3,2-d]pyrimidin-4(3H)-one | 388.09 | 1.3 | * |

TABLE I-continued
Representative 2-Phenoxy Pyrimidinone Derivatives
| | Compound | Name | MS | $R_T$ | $IC_{50}$ |
|---|---|---|---|---|---|
| 33 | 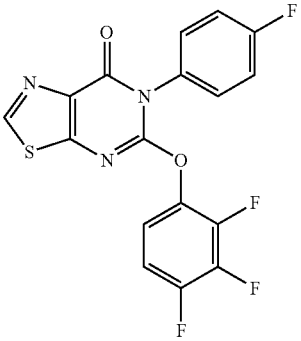 [SMILES: O=c1c2ncsc2nc(Oc2ccc(F)c(F)c2F)n1-c1ccc(F)cc1] | 6-(4-fluorophenyl)-5-(2,3,4-trifluorophenoxy)[1,3]thiazolo[5,4-d]pyrimidin-7(6H)-one | 394.02 | 1.39 | * |
| 34 | 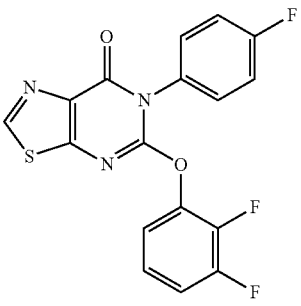 [SMILES: O=c1c2ncsc2nc(Oc2cccc(F)c2F)n1-c1ccc(F)cc1] | 5-(2,3-difluorophenoxy)-6-(4-fluorophenyl)[1,3]thiazolo[5,4-d]pyrimidin-7(6H)-one | 376.02 | 1.27 | * |
| 35 | 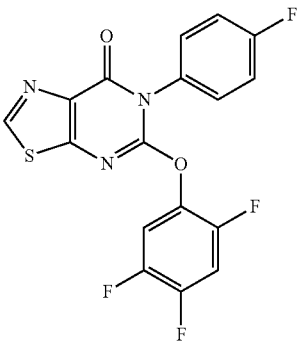 [SMILES: O=c1c2ncsc2nc(Oc2cc(F)c(F)cc2F)n1-c1ccc(F)cc1] | 6-(4-fluorophenyl)-5-(2,4,5-trifluorophenoxy)[1,3]thiazolo[5,4-d]pyrimidin-7(6H)-one | 394.02 | 0.66 | * |
| 36 | 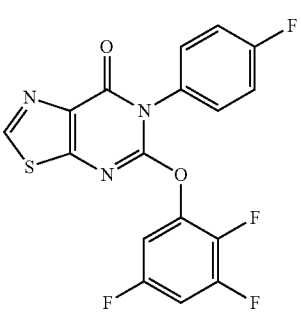 [SMILES: O=c1c2ncsc2nc(Oc2cc(F)cc(F)c2F)n1-c1ccc(F)cc1] | 6-(4-fluorophenyl)-5-(2,3,5-trifluorophenoxy)[1,3]thiazolo[5,4-d]pyrimidin-7(6H)-one | 394.01 | 1.29 | * |

TABLE I-continued

Representative 2-Phenoxy Pyrimidinone Derivatives

| Compound | | Name | MS | $R_T$ | $IC_{50}$ |
|---|---|---|---|---|---|
| 37 | | 6-(4-fluorophenyl)-5-(3,4,5-trifluorophenoxy)[1,3]thiazolo[5,4-d]pyrimidin-7(6H)-one | 394.02 | 1.41 | * |
| 38 | | 5-(4-chloro-2-fluorophenoxy)-6-(4-fluorophenyl)[1,3]thiazolo[5,4-d]pyrimidin-7(6H)-one | 392.00 | 1.09 | * |
| 39 | | 3-(4-fluorophenyl)-2-[3-(trifluoromethyl)phenoxy]pyrido[3,2-d]pyrimidin-4(3H)-one | 402.08 | 1.44 | |
| 40 | | 2-[2-chloro-3-(trifluoromethyl)phenoxy]-3-(4-fluorophenyl)pyrido[3,2-d]pyrimidin-4(3H)-one | 436.04 | 0.51 | |

TABLE I-continued

Representative 2-Phenoxy Pyrimidinone Derivatives

| Compound | | Name | MS | $R_T$ | $IC_{50}$ |
|---|---|---|---|---|---|
| 41 | | 6-(4-fluorophenyl)-5-[2-fluoro-3-(trifluoromethyl)phenoxy][1,3]thiazolo[5,4-d]pyrimidin-7(6H)-one | 426.03 | 0.63 | |
| 42 | | 1-(4-chlorophenyl)-2-[2-fluoro-3-(trifluoromethyl)phenoxy]-9-methyl-1,9-dihydro-6H-purin-6-one | 439.05 | 0.63 | * |
| 43 | | 1-(4-fluorophenyl)-2-[2-fluoro-3-(trifluoromethyl)phenoxy]-9-methyl-1,9-dihydro-6H-purin-6-one | 423.08 | 1.39 | * |
| 44 | | 6-(4-fluorophenyl)-5-[3-fluoro-5-(trifluoromethyl)phenoxy][1,3]thiazolo[5,4-d]pyrimidin-7(6H)-one | 426.03 | 0.51 | * |
| 45 | | 5-[2-chloro-3-(trifluoromethyl)phenoxy]-6-(4-fluorophenyl)[1,3]thiazolo[5,4-d]pyrimidin-7(6H)-one | 442.00 | 0.51 | |

TABLE I-continued

Representative 2-Phenoxy Pyrimidinone Derivatives

| Compound | | Name | MS | $R_T$ | $IC_{50}$ |
|---|---|---|---|---|---|
| 46 | | 6-(4-fluorophenyl)-5-(3-(trifluoromethyl)phenoxy)thiazolo[5,4-d]pyrimidin-7(6H)-one | 408.04 | 1.48 | * |
| 47 | | 3-(4-fluorophenyl)-2-[3-fluoro-5-(trifluoromethyl)phenoxy]pyrido[3,2-d]pyrimidin-4(3H)-one | 420.07 | 0.52 | |
| 48 | | 1-(4-fluorophenyl)-9-methyl-2-[3-(trifluoromethyl)phenoxy]-1,9-dihydro-6H-purin-6-one | 405.09 | 0.54 | * |
| 49 | | 1-(4-fluorophenyl)-2-[3-fluoro-5-(trifluoromethyl)phenoxy]-9-methyl-1,9-dihydro-6H-purin-6-one | 423.08 | 1.36 | * |

TABLE I-continued
Representative 2-Phenoxy Pyrimidinone Derivatives
| Compound | | Name | MS | $R_T$ | $IC_{50}$ |
|---|---|---|---|---|---|
| 50 | 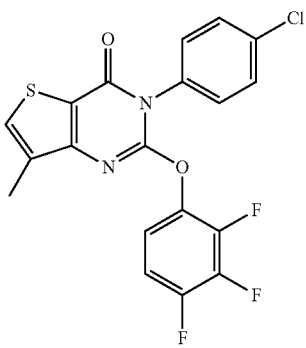 [SMILES: Cc1csc2c(=O)n(-c3ccc(Cl)cc3)c(Oc3ccc(F)c(F)c3F)nc12] | 3-(4-chlorophenyl)-7-methyl-2-(2,3,4-trifluorophenoxy)thieno[3,2-d]pyrimidin-4(3H)-one | 423.03 | 1.4 | * |
| 51 | 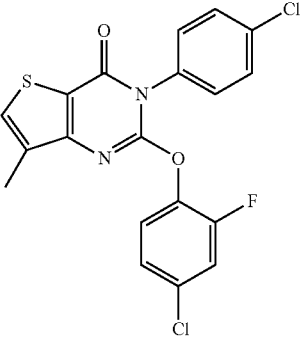 [SMILES: Cc1csc2c(=O)n(-c3ccc(Cl)cc3)c(Oc3ccc(Cl)cc3F)nc12] | 2-(4-chloro-2-fluorophenoxy)-3-(4-chlorophenyl)-7-methylthieno[3,2-d]pyrimidin-4(3H)-one | 421.00 | 1.41 | * |
| 52 | 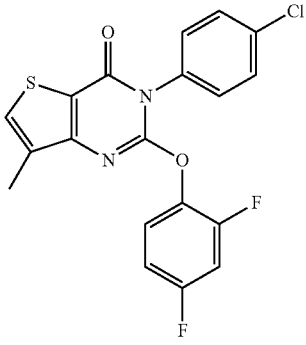 [SMILES: Cc1csc2c(=O)n(-c3ccc(Cl)cc3)c(Oc3ccc(F)cc3F)nc12] | 3-(4-chlorophenyl)-2-(2,4-difluorophenoxy)-7-methylthieno[3,2-d]pyrimidin-4(3H)-one | 405.05 | 1.37 | * |
| 53 | 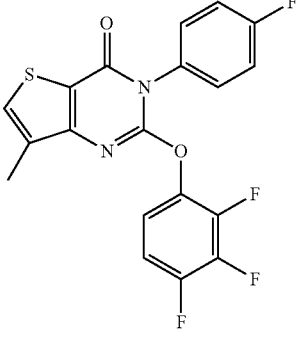 | 3-(4-fluorophenyl)-7-methyl-2-(2,3,4-trifluorophenoxy)thieno[3,2-d]pyrimidin-4(3H)-one | 405.07 | 1.4 | * |

TABLE I-continued

Representative 2-Phenoxy Pyrimidinone Derivatives

| | Compound | Name | MS | R$_T$ | IC$_{50}$ |
|---|---|---|---|---|---|
| 54 | | 2-(4-chloro-2-fluorophenoxy)-3-(4-fluorophenyl)-7-methylthieno[3,2-d]pyrimidin-4(3H)-one | 405.02 | 0.65 | * |
| 55 | | 3-(4-fluorophenyl)-7-methyl-2-(2,3,6-trifluorophenoxy)thieno[3,2-d]pyrimidin-4(3H)-one | 407.07 | 1.36 | * |
| 56 | | 3-(4-fluorophenyl)-4-oxo-2-(2,3,4-trifluorophenoxy)-3,4-dihydrothieno[3,2-d]pyrimidine-7-carbonitrile | 417.99 | 1.31 | |
| 57 | | 3-(4-fluorophenyl)-2-(2-methoxyphenoxy)-7-methylthieno[3,2-d]pyrimidin-4(3H)-one | 383.09 | 1.31 | |

TABLE I-continued

Representative 2-Phenoxy Pyrimidinone Derivatives

| Compound | | Name | MS | R$_T$ | IC$_{50}$ |
|---|---|---|---|---|---|
| 58 | | 3-(4-fluorophenyl)-7-methyl-2-(2-methylphenoxy)thieno[3,2-d]pyrimidin-4(3H)-one | 367.09 | 1.36 | |
| 59 | | 2-(2-ethylphenoxy)-3-(4-fluorophenyl)-7-methylthieno[3,2-d]pyrimidin-4(3H)-one | 381.11 | 1.38 | |
| 60 | | 3-(4-fluorophenyl)-2-(2-isopropylphenoxy)-7-methylthieno[3,2-d]pyrimidin-4(3H)-one | 395.12 | 1.39 | |
| 61 | | 2-(2,3-dimethylphenoxy)-3-(4-fluorophenyl)-7-methylthieno[3,2-d]pyrimidin-4(3H)-one | 413.09 | 1.3 | |
| 62 | | 2-(2,6-dimethylphenoxy)-1-(4-fluorophenyl)-9-methyl-1,9-dihydro-6H-purin-6-one | 365.14 | 1.28 | |

TABLE I-continued

Representative 2-Phenoxy Pyrimidinone Derivatives

| Compound | | Name | MS | $R_T$ | $IC_{50}$ |
|---|---|---|---|---|---|
| 63 | | 2-(2,3-dimethylphenoxy)-1-(4-fluorophenyl)-9-methyl-1,9-dihydro-6H-purin-6-one | 365.13 | 1.28 | * |

Example 4

VR1-Transfected Cells and Membrane Preparations

This Example illustrates the preparation of VR1-transfected cells and VR1-containing membrane preparations for use in capsaicin binding assays (Example 5).

A cDNA encoding full length human capsaicin receptor (SEQ ID NO:1, 2 or 3 of U.S. Pat. No. 6,482,611) is subcloned in the plasmid pBK-CMV (Stratagene, La Jolla, Calif.) for recombinant expression in mammalian cells.

Human embryonic kidney (HEK293) cells are transfected with the pBK-CMV expression construct encoding the full length human capsaicin receptor using standard methods. The transfected cells are selected for two weeks in media containing G418 (400 μg/ml) to obtain a pool of stably transfected cells. Independent clones are isolated from this pool by limiting dilution to obtain clonal stable cell lines for use in subsequent experiments.

For radioligand binding experiments, cells are seeded in T175 cell culture flasks in media without antibiotics and grown to approximately 90% confluency. The flasks are then washed with PBS and harvested in PBS containing 5 mM EDTA. The cells are pelleted by gentle centrifugation and stored at −80° C. until assayed.

Previously frozen cells are disrupted with the aid of a tissue homogenizer in ice-cold HEPES homogenization buffer (5 mM KCl 5, 5.8 mM NaCl, 0.75 mM $CaCl_2$, 2 mM $MgCl_2$, 320 mM sucrose, and 10 mM HEPES pH 7.4). Tissue homogenates are first centrifuged for 10 minutes at 1000×g (4° C.) to remove the nuclear fraction and debris, and then the supernatant from the first centrifugation is further centrifuged for 30 minutes at 35,000×g (4° C.) to obtain a partially purified membrane fraction. Membranes are resuspended in the HEPES homogenization buffer prior to the assay. An aliquot of this membrane homogenate is used to determine protein concentration via the Bradford method (BIO-RAD Protein Assay Kit, #500-0001, BIO-RAD, Hercules, Calif.).

Example 5

Capsaicin Receptor Binding Assay

This Example illustrates a representative assay of capsaicin receptor binding that may be used to determine the binding affinity of compounds for the capsaicin (VR1) receptor.

Binding studies with [$^3$H] Resiniferatoxin (RTX) are carried out essentially as described by Szallasi and Blumberg (1992) J. Pharmacol. Exp. Ter. 262:883-888. In this protocol, non-specific RTX binding is reduced by adding bovine alpha$_1$ acid glycoprotein (100 μg per tube) after the binding reaction has been terminated.

[$^3$H] RTX (37 Ci/mmol) is synthesized by and obtained from the Chemical Synthesis and Analysis Laboratory, National Cancer Institute-Frederick Cancer Research and Development Center, Frederick, Md. [$^3$H] RTX may also be obtained from commercial vendors (e.g., Amersham Pharmacia Biotech, Inc.; Piscataway, N.J.).

The membrane homogenate of Example 4 is centrifuged as before and resuspended to a protein concentration of 333 μg/ml in homogenization buffer. Binding assay mixtures are set up on ice and contain [$^3$H]RTX (specific activity 2200 mCi/ml), 2 μl non-radioactive test compound, 0.25 mg/ml bovine serum albumin (Cohn fraction V), and $5\times10^4$-$1\times10^5$ VR1-transfected cells. The final volume is adjusted to 500 μl (for competition binding assays) or 1,000 μl (for saturation binding assays) with the ice-cold HEPES homogenization buffer solution (pH 7.4) described above. Non-specific binding is defined as that occurring in the presence of 1 μM non-radioactive RTX (Alexis Corp.; San Diego, Calif.). For saturation binding, [$^3$H]RTX is added in the concentration range of 7-1,000 pM, using 1 to 2 dilutions. Typically 11 concentration points are collected per saturation binding curve.

Competition binding assays are performed in the presence of 60 pM [$^3$H]RTX and various concentrations of test compound. The binding reactions are initiated by transferring the assay mixtures into a 37° C. water bath and are terminated following a 60 minute incubation period by cooling the tubes on ice. Membrane-bound RTX is separated from free, as well as any alpha$_1$-acid glycoprotein-bound RTX, by filtration onto WALLAC glass fiber filters (PERKIN-ELMER, Gaithersburg, Md.) which are pre-soaked with 1.0% PEI (polyethyleneimine) for 2 hours prior to use. Filters are allowed to dry overnight then counted in a WALLAC 1205 BETA PLATE counter after addition of WALLAC BETA SCINT scintillation fluid.

Equilibrium binding parameters are determined by fitting the allosteric Hill equation to the measured values with the aid of the computer program FIT P (Biosoft, Ferguson, Mo.) as described by Szallasi, et al. (1993) J. Pharmacol. Exp. Ther. 266:678-683. Compounds provided herein generally exhibit $K_i$ values for capsaicin receptor of less than 1 μM, 100 nM, 50 nM, 25 nM, 10 nM, or 1 nM in this assay.

Example 6

Calcium Mobilization Assay

This Example illustrates representative calcium mobilization assays for use in evaluating test compounds for agonist and antagonist activity.

Cells transfected with expression plasmids (as described in Example 4) and thereby expressing human capsaicin receptor are seeded and grown to 70-90% confluency in FALCON black-walled, clear-bottomed 96-well plates (#3904, BECTON-DICKINSON, Franklin Lakes, N.J.). The culture medium is emptied from the 96 well plates and FLUO-3 AM calcium sensitive dye (Molecular Probes, Eugene, Oreg.) is added to each well (dye solution: 1 mg FLUO-3 AM, 440 μL DMSO and 440 μl 20% pluronic acid in DMSO, diluted 1:250 in Krebs-Ringer HEPES (KRH) buffer (25 mM HEPES, 5 mM KCl, 0.96 mM $NaH_2PO_4$, 1 mM $MgSO_4$, 2 mM $CaCl_2$, 5 mM glucose, 1 mM probenecid, pH 7.4), 50 μl diluted solution per well). Plates are covered with aluminum foil and incubated at 37° C. for 1-2 hours in an environment containing 5% $CO_2$. After the incubation, the dye is emptied from the plates, and the cells are washed once with KRH buffer, and resuspended in KRH buffer.

Determination of Capsaicin $EC_{50}$

To measure the ability of a test compound to agonize or antagonize a calcium mobilization response in cells expressing capsaicin receptors to capsaicin or other vanilloid agonist, the $EC_{50}$ of the agonist capsaicin is first determined. An additional 20 μl of KRH buffer and 1 μl DMSO is added to each well of cells, prepared as described above. 100 μl capsaicin in KRH buffer is automatically transferred by the FLIPR instrument to each well. Capsaicin-induced calcium mobilization is monitored using either FLUOROSKAN ASCENT (Labsystems; Franklin, Mass.) or FLIPR (fluorometric imaging plate reader system; Molecular Devices, Sunnyvale, Calif.) instruments. Data obtained between 30 and 60 seconds after agonist application are used to generate an 8-point concentration response curve, with final capsaicin concentrations of 1 nM to 3 μM. KALEIDAGRAPH software (Synergy Software, Reading, Pa.) is used to fit the data to the equation:

$$y=a*(1/(1+(b/x)^c))$$

to determine the 50% excitatory concentration ($EC_{50}$) for the response. In this equation, y is the maximum fluorescence signal, x is the concentration of the agonist or antagonist (in this case, capsaicin), a is the $E_{max}$, b corresponds to the $EC_{50}$ value and c is the Hill coefficient.

Determination of Agonist Activity

Test compounds are dissolved in DMSO, diluted in KRH buffer, and immediately added to cells prepared as described above. 100 nM capsaicin (an approximate $EC_{90}$ concentration) is also added to cells in the same 96-well plate as a positive control. The final concentration of test compounds in the assay wells is between 0.1 nM and 5 μM.

The ability of a test compound to act as an agonist of the capsaicin receptor is determined by measuring the fluorescence response of cells expressing capsaicin receptors elicited by the compound as function of compound concentration. This data is fit as described above to obtain the $EC_{50}$, which is generally less than 1 micromolar, preferably less than 100 nM, and more preferably less than 10 nM. The extent of efficacy of each test compound is also determined by calculating the response elicited by a concentration of test compound (typically 1 μM) relative to the response elicited by 100 nM capsaicin. This value, called Percent of Signal (POS), is calculated by the following equation:

POS=100*test compound response/100 nM capsaicin response

This analysis provides quantitative assessment of both the potency and efficacy of test compounds as human capsaicin receptor agonists. Agonists of the human capsaicin receptor generally elicit detectable responses at concentrations less than 100 μM, or preferably at concentrations less than 1 μM, or most preferably at concentrations less than 10 nM. Extent of efficacy at human capsaicin receptor is preferably greater than 30 POS, more preferably greater than 80 POS at a concentration of 1 μM. Certain agonists are essentially free of antagonist activity as demonstrated by the absence of detectable antagonist activity in the assay described below at compound concentrations below 4 nM, more preferably at concentrations below 10 μM and most preferably at concentrations less than or equal to 100 μm.

Determination of Antagonist Activity

Test compounds are dissolved in DMSO, diluted in 20 μl KRH buffer so that the final concentration of test compounds in the assay well is between 1 μM and 5 μM, and added to cells prepared as described above. The 96 well plates containing prepared cells and test compounds are incubated in the dark, at room temperature for 0.5 to 6 hours. It is important that the incubation not continue beyond 6 hours. Just prior to determining the fluorescence response, 100 μl capsaicin in KRH buffer at twice the $EC_{50}$ concentration determined as described above is automatically added by the FLIPR instrument to each well of the 96 well plate for a final sample volume of 200 μl and a final capsaicin concentration equal to the $EC_{50}$. The final concentration of test compounds in the assay wells is between 1 μM and 5 μM. Antagonists of the capsaicin receptor decrease this response by at least about 20%, preferably by at least about 50%, and most preferably by at least 80%, as compared to matched control (i.e., cells treated with capsaicin at twice the $EC_{50}$ concentration in the absence of test compound), at a concentration of 10 micromolar or less, preferably 1 micromolar or less. The concentration of antagonist required to provide a 50% decrease, relative to the response observed in the presence of capsaicin and without antagonist, is the $IC_{50}$ for the antagonist, and is preferably below 1 micromolar, 100 nanomolar, 10 nanomolar or 1 nanomolar.

The data is analyzed as follows. First, the average maximum relative fluorescent unit (RFU) response from the negative control wells (no agonist) is subtracted from the maximum response detected for each of the other experimental wells. Second, average maximum RFU response is calculated for the positive control wells (agonist wells). Then, percent inhibition for each compound tested is calculated using the equation:

Percent Inhibition=100−100×(Peak Signal in Test Cells/Peak Signal in Control Cells)

The % inhibition data is plotted as a function of test compound concentration and test compound $IC_{50}$ is determined using, for example, KALEIDAGRAPH software (Synergy Software, Reading, Pa.) best fit of the data to the equation:

$$y=m_1*(1/(1+(m_2/m_0)^{m_3}))$$

where y is the percent inhibition, $m_0$ is the concentration of the agonist, $m_1$ is the maximum RFU, $m_2$ corresponds to the test compound $IC_{50}$ (the concentration required to provide a 50% decrease, relative to the response observed in the presence of agonist and without antagonist) and $m_3$ is the Hill coefficient. Alternatively, test compound $IC_{50}$ is determined using a linear regression in which x is ln(concentration of test compound) and y is ln(percent inhibition/(100−percent inhibition). Data with a percent inhibition that is greater than 90% or less than 15% are rejected and are not used in the regression. The $IC_{50}$ calculated in this fashion is $e^{(-intercept/slope)}$.

Certain preferred VR1 modulators are antagonists that are essentially free of agonist activity as demonstrated by the absence of detectable agonist activity in the assay described above at compound concentrations below 4 nM, more preferably at concentrations below 10 μM and most preferably at concentrations less than or equal to 100 μM.

Example 7

Dorsal Root Ganglion Cell Assay

This Example illustrates a representative dorsal root ganglian cell assay for evaluating VR1 antagonist or agonist activity of a compound.

DRG are dissected from neonatal rats, dissociated and cultured using standard methods (Aguayo and White (1992) *Brain Research* 570:61-67). After 48 hour incubation, cells are washed once and incubated for 30-60 minutes with the calcium sensitive dye Fluo 4 AM (2.5-10 ug/ml; TefLabs, Austin, Tex.). Cells are then washed once. Addition of capsaicin to the cells results in a VR1-dependent increase in intracellular calcium levels which is monitored by a change in Fluo-4 fluorescence with a fluorometer. Data are collected for 60-180 seconds to determine the maximum fluorescent signal.

For antagonist assays, various concentrations of compound are added to the cells. Fluorescent signal is then plotted as a function of compound concentration to identify the concentration required to achieve a 50% inhibition of the capsaicin-activated response, or $IC_{50}$. Antagonists of the capsaicin receptor preferably have an $IC_{50}$ below 1 micromolar, 100 nanomolar, 10 nanomolar or 1 nanomolar. For agonist assays, various concentrations of compound are added to the cells without the addition of capsaicin. Compounds that are capsaicin receptor agonists result in a VR1-dependent increase in intracellular calcium levels which is monitored by a change in Fluo-4 fluorescence with a fluorometer. The $EC_{50}$, or concentration required to achieve 50% of the maximum signal for a capsaicin-activated response, is preferably below 1 micromolar, below 100 nanomolar or below 10 nanomolar.

Example 8

Animal Models for Determining Pain Relief

This Example illustrates representative methods for assessing the degree of pain relief provided by a compound.
A. Pain Relief Testing
The following methods may be used to assess pain relief.
Mechanical Allodynia
Mechanical allodynia (an abnormal response to an innocuous stimulus) is assessed essentially as described by Chaplan et al. (1994) *J. Neurosci. Methods* 53:55-63 and Tal and Eliav (1998) *Pain* 64(3):511-518. A series of von Frey filaments of varying rigidity (typically 8-14 filaments in a series) are applied to the plantar surface of the hind paw with just enough force to bend the filament. The filaments are held in this position for no more than three seconds or until a positive allodynic response is displayed by the rat. A positive allodynic response consists of lifting the affected paw followed immediately by licking or shaking of the paw. The order and frequency with which the individual filaments are applied are determined by using Dixon up-down method. Testing is initiated with the middle hair of the series with subsequent filaments being applied in consecutive fashion, ascending or descending, depending on whether a negative or positive response, respectively, is obtained with the initial filament.

Compounds are effective in reversing or preventing mechanical allodynia-like symptoms if rats treated with such compounds require stimulation with a Von Frey filament of higher rigidity strength to provoke a positive allodynic response as compared to control untreated or vehicle treated rats. Alternatively, or in addition, testing of an animal in chronic pain may be done before and after compound administration. In such an assay, an effective compound results in an increase in the rigidity of the filament needed to induce a response after treatment, as compared to the filament that induces a response before treatment or in an animal that is also in chronic pain but is left untreated or is treated with vehicle. Test compounds are administered before or after onset of pain. When a test compound is administered after pain onset, testing is performed 10 minutes to three hours after administration.
Mechanical Hyperalgesia
Mechanical hyperalgesia (an exaggerated response to painful stimulus) is tested essentially as described by Koch et al. (1996) *Analgesia* 2(3):157-164. Rats are placed in individual compartments of a cage with a warmed, perforated metal floor. Hind paw withdrawal duration (i.e., the amount of time for which the animal holds its paw up before placing it back on the floor) is measured after a mild pinprick to the plantar surface of either hind paw.

Compounds produce a reduction in mechanical hyperalgesia if there is a statistically significant decrease in the duration of hindpaw withdrawal. Test compound may be administered before or after onset of pain. For compounds administered after pain onset, testing is performed 10 minutes to three hours after administration.
Thermal Hyperalgesia
Thermal hyperalgesia (an exaggerated response to noxious thermal stimulus) is measured essentially as described by Hargreaves et al. (1988) *Pain*. 32(1):77-88. Briefly, a constant radiant heat source is applied the animals' plantar surface of either hind paw. The time to withdrawal (i.e., the amount of time that heat is applied before the animal moves its paw), otherwise described as thermal threshold or latency, determines the animal's hind paw sensitivity to heat.

Compounds produce a reduction in thermal hyperalgesia if there is a statistically significant increase in the time to hindpaw withdrawal (i.e., the thermal threshold to response or latency is increased). Test compound may be administered before or after onset of pain. For compounds administered after pain onset, testing is performed 10 minutes to three hours after administration.
B. Pain Models
Pain may be induced using any of the following methods, to allow testing of analgesic efficacy of a compound. In general, compounds provided herein result in a statistically significant reduction in pain as determined by at least one of the previously described testing methods, using male SD rats and at least one of the following models.
Acute Inflammatory Pain Model
Acute inflammatory pain is induced using the carrageenan model essentially as described by Field et al. (1997) *Br. J. Pharmacol*. 121(8):1513-1522. 100-200 μl of 1-2% carrageenan solution is injected into the rats' hind paw. Three to four hours following injection, the animals' sensitivity to thermal and mechanical stimuli is tested using the methods described above. A test compound (0.01 to 50 mg/kg) is administered to the animal, prior to testing, or prior to injection of carrageenan. The compound can be administered orally or through any parenteral route, or topically on the paw. Compounds that relieve pain in this model result in a statistically significant reduction in mechanical allodynia and/or thermal hyperalgesia.

Chronic Inflammatory Pain Model

Chronic inflammatory pain is induced using one of the following protocols:
1. Essentially as described by Bertorelli et al. (1999) *Br. J. Pharmacol.* 128(6):1252-1258, and Stein et al. (1998) *Pharmacol. Biochem. Behav.* 31(2):455-51, 200 μl Complete Freund's Adjuvant (0.1 mg heat killed and dried *M. Tuberculosis*) is injected to the rats' hind paw: 100 μl into the dorsal surface and 100 μl into the plantar surface.
2. Essentially as described by Abbadie et al. (1994) *J Neurosci.* 14(10):5865-5871 rats are injected with 150 μl of CFA (1.5 mg) in the tibio-tarsal joint.

Prior to injection with CFA in either protocol, an individual baseline sensitivity to mechanical and thermal stimulation of the animals' hind paws is obtained for each experimental animal.

Following injection of CFA, rats are tested for thermal hyperalgesia, mechanical allodynia and mechanical hyperalgesia as described above. To verify the development of symptoms, rats are tested on days 5, 6, and 7 following CFA injection. On day 7, animals are treated with a test compound, morphine or vehicle. An oral dose of morphine of 1-5 mg/kg is suitable as positive control. Typically, a dose of 0.01-50 mg/kg of test compound is used. Compounds can be administered as a single bolus prior to testing or once or twice or three times daily, for several days prior to testing. Drugs are administered orally or through any parenteral route, or applied topically to the animal.

Results are expressed as Percent Maximum Potential Efficacy (MPE). 0% MPE is defined as analgesic effect of vehicle, 100% MPE is defined as an animal's return to pre-CFA baseline sensitivity. Compounds that relieve pain in this model result in a MPE of at least 30%.

Chronic Neuropathic Pain Model

Chronic neuropathic pain is induced using the chronic constriction injury (CCI) to the rat's sciatic nerve essentially as described by Bennett and Xie (1988) *Pain* 33:87-107. Rats are anesthetized (e.g. with an intraperitoneal dose of 50-65 mg/kg pentobarbital with additional doses administered as needed). The lateral aspect of each hind limb is shaved and disinfected. Using aseptic technique, an incision is made on the lateral aspect of the hind limb at the mid thigh level. The biceps femoris is bluntly dissected and the sciatic nerve is exposed. On one hind limb of each animal, four loosely tied ligatures are made around the sciatic nerve approximately 1-2 mm apart. On the other side the sciatic nerve is not ligated and is not manipulated. The muscle is closed with continuous pattern and the skin is closed with wound clips or sutures. Rats are assessed for mechanical allodynia, mechanical hyperalgesia and thermal hyperalgesia as described above.

Compounds that relieve pain in this model result in a statistically significant reduction in mechanical allodynia, mechanical hyperalgesia and/or thermal hyperalgesia when administered (0.01-50 mg/kg, orally, parenterally or topically) immediately prior to testing as a single bolus, or for several days: once or twice or three times daily prior to testing.

What is claimed is:

1. A method for treating pain in a patient, comprising administering to a patient suffering from pain a therapeutically effective amount of at least one compound of the formula:

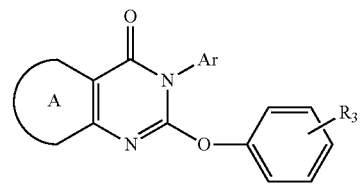

or a pharmaceutically acceptable salt or hydrate thereof, wherein:

represents

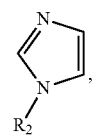

wherein $R_2$ is hydrogen, $C_1$-$C_4$alkyl, $C_1$-$C_4$haloalkyl or $C_3$-$C_5$cycloalkyl;

Ar is phenyl or a 5- or 6-membered heteroaryl, each of which is substituted with from 0 to 4 substituents that are independently chosen from halogen, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, $(C_3$-$C_7$cycloalkyl)$C_0$-$C_4$alkyl, and mono- or di-($C_1$-$C_6$alkyl)amino; and $R_3$ represents from 0 to 4 substituents that are independently chosen from halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, $(C_3$-$C_7$cycloalkyl)$C_0$-$C_4$alkyl, mono- or di-($C_1$-$C_6$alkyl)amino, and mono- or di-($C_1$-$C_6$alkyl)aminosulfonyl, and thereby alleviating pain in the patient.

2. A method for treating itch in a patient, comprising administering to a patient a therapeutically effective amount of a compound of the formula:

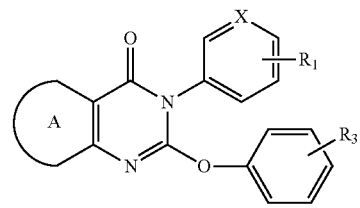

or a pharmaceutically acceptable salt or hydrate thereof, wherein:

represents

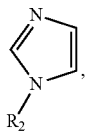

wherein $R_2$ is hydrogen, $C_1$-$C_4$alkyl, $C_1$-$C_4$haloalkyl or $C_3$-$C_5$cycloalkyl;

Ar is phenyl or a 5- or 6-membered heteroaryl, each of which is substituted with from 0 to 4 substituents that are independently chosen from halogen, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, $(C_3$-$C_7$cycloalkyl)$C_0$-$C_4$alkyl, and mono- or di-($C_1$-$C_6$alkyl)amino; and $R_3$ represents from 0 to 4 substituents that are independently chosen from halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, $(C_3$-$C_7$cycloalkyl)$C_0$-$C_4$alkyl, mono- or di-($C_1$-$C_6$alkyl)amino, and mono- or di-($C_1$-$C_6$alkyl)aminosulfonyl, and thereby alleviating itch in the patient.

3. A method for treating cough or hiccup in a patient, comprising administering to a patient a therapeutically effective amount of a compound of the formula:

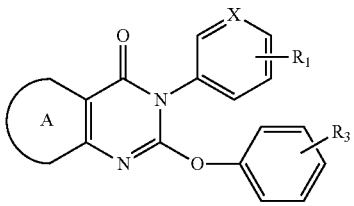

or a pharmaceutically acceptable salt or hydrate thereof, wherein:

represents

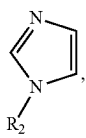

wherein $R_2$ is hydrogen, $C_1$-$C_4$alkyl, $C_1$-$C_4$haloalkyl or $C_3$-$C_5$cycloalkyl;

Ar is phenyl or a 5- or 6-membered heteroaryl, each of which is substituted with from 0 to 4 substituents that are independently chosen from halogen, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, $(C_3$-$C_7$cycloalkyl)$C_0$-$C_4$alkyl, and mono- or di-($C_1$-$C_6$alkyl)amino; and $R_3$ represents from 0 to 4 substituents that are independently chosen from halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, $(C_3$-$C_7$cycloalkyl)$C_0$-$C_4$alkyl, mono- or di-($C_1$-$C_6$alkyl)amino, and mono- or di-($C_1$-$C_6$alkyl)aminosulfonyl, and thereby alleviating cough or hiccup in the patient.

4. A method for treating urinary incontinence or overactive bladder in a patient, comprising administering to a patient a therapeutically effective amount of a compound of the formula:

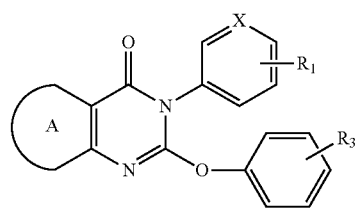

or a pharmaceutically acceptable salt or hydrate thereof, wherein:

represents

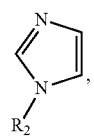

wherein $R_2$ is hydrogen, $C_1$-$C_4$haloalkyl or $C_3$-$C_5$cycloalkyl;

Ar is phenyl or a 5- or 6-membered heteroaryl, each of which is substituted with from 0 to 4 substituents that are independently chosen from halogen, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, $(C_3$-$C_7$cycloalkyl)$C_0$-$C_4$alkyl, and mono- or di-($C_1$-$C_6$alkyl)amino; and $R_3$ represents from 0 to 4 substituents that are independently chosen from halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, $(C_3$-$C_7$cycloalkyl)$C_0$-$C_4$alkyl, mono- or di-($C_1$-$C_6$alkyl)amino, and mono- or di-($C_1$-$C_6$alkyl)aminosulfonyl, and thereby alleviating urinary incontinence or overactive bladder in the patient.

5. A method for treating pain in a patient, comprising administering to a patient suffering from pain a therapeutically effective amount of a combination of (i) at least one compound of the formula:

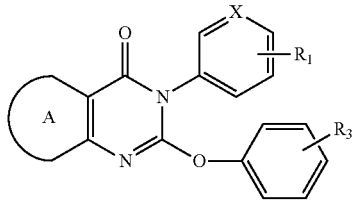

or a pharmaceutically acceptable salt or hydrate thereof, wherein:

represents

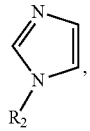

wherein $R_2$ is hydrogen, $C_1$-$C_4$alkyl, $C_1$-$C_4$haloalkyl or $C_3$-$C_5$cycloalkyl;
Ar is phenyl or a 5- or 6-membered heteroaryl, each of which is substituted with from 0 to 4 substituents that are independently chosen from halogen, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, $(C_3$-$C_7$cycloalkyl)$C_0$-$C_4$alkyl, and mono- or di-($C_1$-$C_6$alkyl)amino; and
$R_3$ represents from 0 to 4 substituents that are independently chosen from halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, $(C_3$-$C_7$cycloalkyl)$C_0$-$C_4$alkyl, mono- or di-($C_1$-$C_6$alkyl)amino, and mono- or di-($C_1$-$C_6$alkyl)aminosulfonyl, and (ii) ibuprofen, and thereby alleviating pain in the patient.

6. The method of claim 1, wherein, in the compound or salt or hydrate thereof, $R_3$ represents from 1 to 3 substituents independently chosen from halogen, cyano, $C_1$-$C_6$alkyl, $C_1$-$C_6$haloalkyl and $C_1$-$C_6$alkoxy.

7. The method of claim 1, wherein the compound or salt or hydrate thereof has the formula:

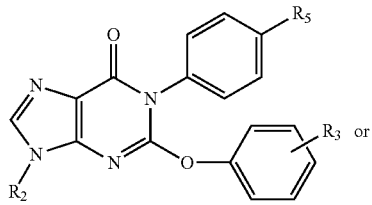

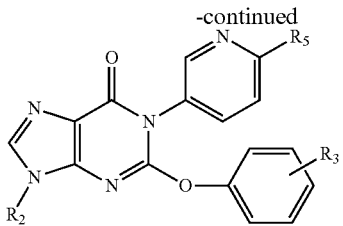

wherein:
$R_2$ is hydrogen, $C_1$-$C_4$alkyl, $C_1$-$C_4$haloalkyl or $C_3$-$C_5$cycloalkyl;
$R_3$ represents from 1 to 3 substituents independently chosen from halogen, cyano, $C_1$-$C_4$alkyl, $C_1$-$C_4$haloalkyl and $C_1$-$C_4$alkoxy; and
$R_5$ is halogen or CN.

8. The method of claim 1, wherein the compound is:
1-(4-bromophenyl)-9-methyl-2-(2,3,4-trifluorophenoxy)-1,9-dihydro-6H-purin-6-one;
1-(4-chlorophenyl)-2-(2,3-difluorophenoxy)-9-methyl-1,9-dihydro-6H-purin-6-one;
1-(4-chlorophenyl)-2-(2,4-difluorophenoxy)-9-methyl-1,9-dihydro-6H-purin-6-one;
1-(4-chlorophenyl)-2-[2-fluoro-3-(trifluoromethyl)phenoxy]-9-methyl-1,9-dihydro-6H-purin-6-one;
1-(4-chlorophenyl)-9-methyl-2-(2,3,4-trifluorophenoxy)-1,9-dihydro-6H-purin-6-one;
1-(4-chlorophenyl)-9-methyl-2-(2,3,5-trifluorophenoxy)-1,9-dihydro-6H-purin-6-one;
1-(4-chlorophenyl)-9-methyl-2-(2,3,6-trifluorophenoxy)-1,9-dihydro-6H-purin-6-one;
1-(4-chlorophenyl)-9-methyl-2-(2,4,5-trifluorophenoxy)-1,9-dihydro-6H-purin-6-one;
1-(4-chlorophenyl)-9-methyl-2-(2,4,6-trifluorophenoxy)-1,9-dihydro-6H-purin-6-one;
1-(4-chlorophenyl)-9-methyl-2-(3,4,5-trifluorophenoxy)-1,9-dihydro-6H-purin-6-one;
1-(4-fluorophenyl)-2-[2-fluoro-3-(trifluoromethyl)phenoxy]-9-methyl-1,9-dihydro-6H-purin-6-one;
1-(4-fluorophenyl)-2-[3-fluoro-5-(trifluoromethyl)phenoxy]-9-methyl-1,9-dihydro-6H-purin-6-one;
1-(4-fluorophenyl)-9-methyl-2-(2,3,4-trifluorophenoxy)-1,9-dihydro-6H-purin-6-one;
1-(4-fluorophenyl)-9-methyl-2-(2,3,5-trifluorophenoxy)-1,9-dihydro-6H-purin-6-one;
1-(4-fluorophenyl)-9-methyl-2-(2,3,6-trifluorophenoxy)-1,9-dihydro-6H-purin-6-one;
1-(4-fluorophenyl)-9-methyl-2-(2,4,5-trifluorophenoxy)-1,9-dihydro-6H-purin-6-one;
1-(4-fluorophenyl)-9-methyl-2-(2,4,6-trifluorophenoxy)-1,9-dihydro-6H-purin-6-one;
1-(4-fluorophenyl)-9-methyl-2-[3-(trifluoromethyl)phenoxy]-1,9-dihydro-6H-purin-6-one;
1-(6-chloropyridin-3-yl)-9-methyl-2-(3,4,5-trifluorophenoxy)-1H-purin-6(9H)-one;
2-(2,3-difluoro-4-methoxyphenoxy)-1-(4-fluorophenyl)-9-methyl-1,9-dihydro-6H-purin-6-one;
2-(2,3-difluoro-4-methoxyphenoxy)-9-ethyl-1-(4-fluorophenyl)-1,9-dihydro-6H-purin-6-one;
2-(2,3-difluorophenoxy)-1-(4-fluorophenyl)-9-methyl-1,9-dihydro-6H-purin-6-one;
2-(2,3-difluorophenoxy)-9-ethyl-1-(4-fluorophenyl)-1,9-dihydro-6H-purin-6-one;
2-(2,3-dimethylphenoxy)-1-(4-fluorophenyl)-9-methyl-1,9-dihydro-6H-purin-6-one;

2-(2,4-difluorophenoxy)-1-(4-fluorophenyl)-9-methyl-1,9-dihydro-6H-purin-6-one;
2-(2,4-difluorophenoxy)-3-(4-fluorophenyl)pyrido[3,2-d]pyrimidin-4(3H)-one;
2-(2,4-difluorophenoxy)-9-ethyl-1-(4-fluorophenyl)-1,9-dihydro-6H-purin-6-one;
2-(2,6-dimethylphenoxy)-1-(4-fluorophenyl)-9-methyl-1,9-dihydro-6H-purin-6-one;
2-(2-chloro-4-fluorophenoxy)-1-(4-chlorophenyl)-9-methyl-1,9-dihydro-6H-purin-6-one;
2-(2-chloro-4-fluorophenoxy)-1-(4-fluorophenyl)-9-methyl-1,9-dihydro-6H-purin-6-one;
2-(4-chloro-2-fluorophenoxy)-1-(4-chlorophenyl)-9-methyl-1,9-dihydro-6H-purin-6-one;
2-(4-chloro-2-fluorophenoxy)-1-(4-fluorophenyl)-9-methyl-1,9-dihydro-6H-purin-6-one;
2-(4-chloro-2-fluorophenoxy)-9-ethyl-1-(4-fluorophenyl)-1,9-dihydro-6H-purin-6-one;
2,3-difluoro-4-{[1-(4-fluorophenyl)-9-methyl-6-oxo-6,9-dihydro-1H-purin-2-yl]oxy}benzonitrile;
4-{([1-(4-chlorophenyl)-9-methyl-6-oxo-6,9-dihydro-1H-purin-2-yl]oxy}-2,3-difluorobenzonitrile;
5-(9-Methyl-6-oxo-2-(3,4,5-trifluorophenoxy)-6H-purin-1(9H)-yl)picolinonitrile;
5-[2-chloro-3-(trifluoromethyl)phenoxy]-6-(4-fluorophenyl)[1,3]thiazolo[5,4-d]pyrimidin-7(6H)-one;
9-ethyl-1-(4-fluorophenyl)-2-(2,3,4-trifluorophenoxy)-1,9-dihydro-6H-purin-6-one;
9-ethyl-1-(4-fluorophenyl)-2-(2,3,5-trifluorophenoxy)-1,9-dihydro-6H-purin-6-one;
9-ethyl-1-(4-fluorophenyl)-2-(2,4,5-trifluorophenoxy)-1,9-dihydro-6H-purin-6-one; or
9-ethyl-1-(4-fluorophenyl)-2-(2,4,6-trifluorophenoxy)-1,9-dihydro-6H-purin-6-one.

9. The method of claim 2, wherein, in the compound or salt or hydrate thereof, $R_3$ represents from 1 to 3 substituents independently chosen from halogen, cyano, $C_1$-$C_6$alkyl, $C_1$-$C_6$haloalkyl and $C_1$-$C_6$alkoxy.

10. The method of claim 2, wherein the compound or salt or hydrate thereof has the formula:

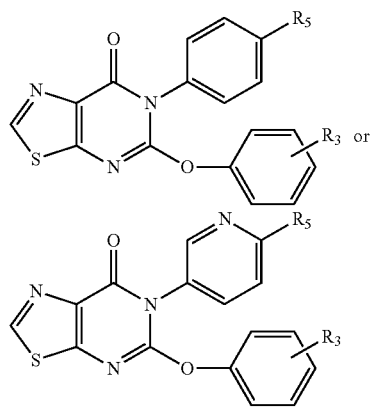

wherein:
$R_2$ is hydrogen, $C_1$-$C_4$alkyl, $C_1$-$C_4$haloalkyl or $C_3$-$C_5$cycloalkyl;
$R_3$ represents from 1 to 3 substituents independently chosen from halogen, cyano, $C_1$-$C_4$alkyl, $C_1$-$C_4$haloalkyl and $C_1$-$C_4$alkoxy; and
$R_5$ is halogen or CN.

11. The method of claim 2, wherein the compound is:
1-(4-bromophenyl)-9-methyl-2-(2,3,4-trifluorophenoxy)-1,9-dihydro-6H-purin-6-one;
1-(4-chlorophenyl)-2-(2,3-difluorophenoxy)-9-methyl-1,9-dihydro-6H-purin-6-one;
1-(4-chlorophenyl)-2-(2,4-difluorophenoxy)-9-methyl-1,9-dihydro-6H-purin-6-one;
1-(4-chlorophenyl)-2-[2-fluoro-3-(trifluoromethyl)phenoxy]-9-methyl-1,9-dihydro-6H-purin-6-one;
1-(4-chlorophenyl)-9-methyl-2-(2,3,4-trifluorophenoxy)-1,9-dihydro-6H-purin-6-one;
1-(4-chlorophenyl)-9-methyl-2-(2,3,5-trifluorophenoxy)-1,9-dihydro-6H-purin-6-one;
1-(4-chlorophenyl)-9-methyl-2-(2,3,6-trifluorophenoxy)-1,9-dihydro-6H-purin-6-one;
1-(4-chlorophenyl)-9-methyl-2-(2,4,5-trifluorophenoxy)-1,9-dihydro-6H-purin-6-one;
1-(4-chlorophenyl)-9-methyl-2-(2,4,6-trifluorophenoxy)-1,9-dihydro-6H-purin-6-one;
1-(4-chlorophenyl)-9-methyl-2-(3,4,5-trifluorophenoxy)-1,9-dihydro-6H-purin-6-one;
1-(4-fluorophenyl)-2-[2-fluoro-3-(trifluoromethyl)phenoxy]-9-methyl-1,9-dihydro-6H-purin-6-one;
1-(4-fluorophenyl)-2-[3-fluoro-5-(trifluoromethyl)phenoxy]-9-methyl-1,9-dihydro-6H-purin-6-one;
1-(4-fluorophenyl)-9-methyl-2-(2,3,4-trifluorophenoxy)-1,9-dihydro-6H-purin-6-one;
1-(4-fluorophenyl)-9-methyl-2-(2,3,5-trifluorophenoxy)-1,9-dihydro-6H-purin-6-one;
1-(4-fluorophenyl)-9-methyl-2-(2,3,6-trifluorophenoxy)-1,9-dihydro-6H-purin-6-one;
1-(4-fluorophenyl)-9-methyl-2-(2,4,5-trifluorophenoxy)-1,9-dihydro-6H-purin-6-one;
1-(4-fluorophenyl)-9-methyl-2-(2,4,6-trifluorophenoxy)-1,9-dihydro-6H-purin-6-one;
1-(4-fluorophenyl)-9-methyl-2-[3-(trifluoromethyl)phenoxy]-1,9-dihydro-6H-purin-6-one;
1-(6-chloropyridin-3-yl)-9-methyl-2-(3,4,5-trifluorophenoxy)-1H-purin-6(9H)-one;
2-(2,3-difluoro-4-methoxyphenoxy)-1-(4-fluorophenyl)-9-methyl-1,9-dihydro-6H-purin-6-one;
2-(2,3-difluoro-4-methoxyphenoxy)-9-ethyl-1-(4-fluorophenyl)-1,9-dihydro-6H-purin-6-one;
2-(2,3-difluorophenoxy)-1-(4-fluorophenyl)-9-methyl-1,9-dihydro-6H-purin-6-one;
2-(2,3-difluorophenoxy)-9-ethyl-1-(4-fluorophenyl)-1,9-dihydro-6H-purin-6-one;
2-(2,3-dimethylphenoxy)-1-(4-fluorophenyl)-9-methyl-1,9-dihydro-6H-purin-6-one;
2-(2,4-difluorophenoxy)-1-(4-fluorophenyl)-9-methyl-1,9-dihydro-6H-purin-6-one;
2-(2,4-difluorophenoxy)-3-(4-fluorophenyl)pyrido[3,2-d]pyrimidin-4(3H)-one;
2-(2,4-difluorophenoxy)-9-ethyl-1-(4-fluorophenyl)-1,9-dihydro-6H-purin-6-one;
2-(2,6-dimethylphenoxy)-1-(4-fluorophenyl)-9-methyl-1,9-dihydro-6H-purin-6-one;
2-(2-chloro-4-fluorophenoxy)-1-(4-chlorophenyl)-9-methyl-1,9-dihydro-6H-purin-6-one;
2-(2-chloro-4-fluorophenoxy)-1-(4-fluorophenyl)-9-methyl-1,9-dihydro-6H-purin-6-one;
2-(4-chloro-2-fluorophenoxy)-1-(4-chlorophenyl)-9-methyl-1,9-dihydro-6H-purin-6-one;
2-(4-chloro-2-fluorophenoxy)-1-(4-fluorophenyl)-9-methyl-1,9-dihydro-6H-purin-6-one;
2-(4-chloro-2-fluorophenoxy)-9-ethyl-1-(4-fluorophenyl)-1,9-dihydro-6H-purin-6-one;

2,3-difluoro-4-{([1-(4-fluorophenyl)-9-methyl-6-oxo-6,9-dihydro-1H-purin-2-yl]oxy}benzonitrile;
4-{([1-(4-chlorophenyl)-9-methyl-6-oxo-6,9-dihydro-1H-purin-2-yl]oxy}-2,3-difluorobenzonitrile;
5-(9-Methyl-6-oxo-2-(3,4,5-trifluorophenoxy)-6H-purin-1(9H)-yl)picolinonitrile;
5-[2-chloro-3-(trifluoromethyl)phenoxy]-6-(4-fluorophenyl)[1,3]thiazolo[5,4-d]pyrimidin-7(6H)-one;
9-ethyl-1-(4-fluorophenyl)-2-(2,3,4-trifluorophenoxy)-1,9-dihydro-6H-purin-6-one;
9-ethyl-1-(4-fluorophenyl)-2-(2,3,5-trifluorophenoxy)-1,9-dihydro-6H-purin-6-one;
9-ethyl-1-(4-fluorophenyl)-2-(2,4,5-trifluorophenoxy)-1,9-dihydro-6H-purin-6-one; or
9-ethyl-1-(4-fluorophenyl)-2-(2,4,6-trifluorophenoxy)-1,9-dihydro-6H-purin-6-one.

12. The method of claim 4, wherein, in the compound or salt or hydrate thereof, $R_3$ represents from 1to 3 substituents independently chosen from halogen, cyano, $C_1$-$C_6$alkyl, $C_1$-$C_6$haloalkyl and $C_1$-$C_6$alkoxy.

13. The method of claim 4, wherein the compound or salt or hydrate thereof has the formula:

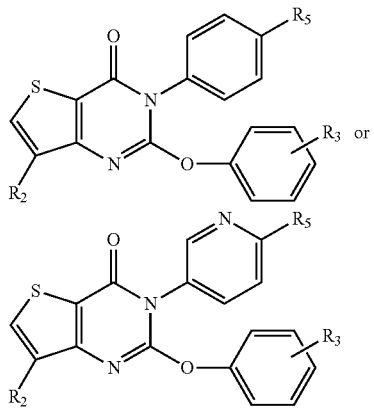

wherein:
$R_2$ is hydrogen, $C_1$-$C_4$alkyl, $C_1$-$C_4$haloalkyl or $C_3$-$C_5$cycloalkyl;
$R_3$ represents from 1to 3 substituents independently chosen from halogen, cyano, $C_1$-$C_4$alkyl, $C_1$-$C_4$haloalkyl and $C_1$-$C_4$alkoxy; and
$R_5$ is halogen or CN.

14. The method of claim 4, wherein the compound is:
1-(4-bromophenyl)-9-methyl-2-(2,3,4-trifluorophenoxy)-1,9-dihydro-6H-purin-6-one;
1-(4-chlorophenyl)-2-(2,3-difluorophenoxy)-9-methyl-1,9-dihydro-6H-purin-6-one;
1-(4-chlorophenyl)-2-(2,4-difluorophenoxy)-9-methyl-1,9-dihydro-6H-purin-6-one;
1-(4-chlorophenyl)-2-[2-fluoro-3-(trifluoromethyl)phenoxy]-9-methyl-1,9-dihydro-6H-purin-6-one;
1-(4-chlorophenyl)-9-methyl-2-(2,3,4-trifluorophenoxy)-1,9-dihydro-6H-purin-6-one;
1-(4-chlorophenyl)-9-methyl-2-(2,3,5-trifluorophenoxy)-1,9-dihydro-6H-purin-6-one;
1-(4-chlorophenyl)-9-methyl-2-(2,3,6-trifluorophenoxy)-1,9-dihydro-6H-purin-6-one;
1-(4-chlorophenyl)-9-methyl-2-(2,4,5-trifluorophenoxy)-1,9-dihydro-6H-purin-6-one;
1-(4-chlorophenyl)-9-methyl-2-(2,4,6-trifluorophenoxy)-1,9-dihydro-6H-purin-6-one;
1-(4-chlorophenyl)-9-methyl-2-(3,4,5-trifluorophenoxy)-1,9-dihydro-6H-purin-6-one;
1-(4-fluorophenyl)-2-[2-fluoro-3-(trifluoromethyl)phenoxy]-9-methyl-1,9-dihydro-6H-purin-6-one;
1-(4-fluorophenyl)-2-[3-fluoro-5-(trifluoromethyl)phenoxy]-9-methyl-1,9-dihydro-6H-purin-6-one;
1-(4-fluorophenyl)-9-methyl-2-(2,3,4-trifluorophenoxy)-1,9-dihydro-6H-purin-6-one;
1-(4-fluorophenyl)-9-methyl-2-(2,3,5-trifluorophenoxy)-1,9-dihydro-6H-purin-6-one;
1-(4-fluorophenyl)-9-methyl-2-(2,3,6-trifluorophenoxy)-1,9-dihydro-6H-purin-6-one;
1-(4-fluorophenyl)-9-methyl-2-(2,4,5-trifluorophenoxy)-1,9-dihydro-6H-purin-6-one;
1-(4-fluorophenyl)-9-methyl-2-(2,4,6-trifluorophenoxy)-1,9-dihydro-6H-purin-6-one;
1-(4-fluorophenyl)-9-methyl-2-[3-(trifluoromethyl)phenoxy]-1,9-dihydro-6H-purin-6-one;
1-(6-chloropyridin-3-yl)-9-methyl-2-(3,4,5-trifluorophenoxy)-1H-purin-6(9H)-one;
2-(2,3-difluoro-4-methoxyphenoxy)-1-(4-fluorophenyl)-9-methyl-1,9-dihydro-6H-purin-6-one;
2-(2,3-difluoro-4-methoxyphenoxy)-9-ethyl-1-(4-fluorophenyl)-1,9-dihydro-6H-purin-6-one;
2-(2,3-difluorophenoxy)-1-(4-fluorophenyl)-9-methyl-1,9-dihydro-6H-purin-6-one;
2-(2,3-difluorophenoxy)-9-ethyl-1-(4-fluorophenyl)-1,9-dihydro-6H-purin-6-one;
2-(2,3-dimethylphenoxy)-1-(4-fluorophenyl)-9-methyl-1,9-dihydro-6H-purin-6-one;
2-(2,4-difluorophenoxy)-1-(4-fluorophenyl)-9-methyl-1,9-dihydro-6H-purin-6-one;
2-(2,4-difluorophenoxy)-3-(4-fluorophenyl)pyrido[3,2-d]pyrimidin-4(3H)-one;
2-(2,4-difluorophenoxy)-9-ethyl-1-(4-fluorophenyl)-1,9-dihydro-6H-purin-6-one;
2-(2,6-dimethylphenoxy)-1-(4-fluorophenyl)-9-methyl-1,9-dihydro-6H-purin-6-one;
2-(2-chloro-4-fluorophenoxy)-1-(4-chlorophenyl)-9-methyl-1,9-dihydro-6H-purin-6-one;
2-(2-chloro-4-fluorophenoxy)-1-(4-fluorophenyl)-9-methyl-1,9-dihydro-6H-purin-6-one;
2-(4-chloro-2-fluorophenoxy)-1-(4-chlorophenyl)-9-methyl-1,9-dihydro-6H-purin-6-one;
2-(4-chloro-2-fluorophenoxy)-1-(4-fluorophenyl)-9-methyl-1,9-dihydro-6H-purin-6-one;
2-(4-chloro-2-fluorophenoxy)-9-ethyl-1-(4-fluorophenyl)-1,9-dihydro-6H-purin-6-one;
2,3-difluoro-4-{([1-(4-fluorophenyl)-9-methyl-6-oxo-6,9-dihydro-1H-purin-2-yl]oxy}benzonitrile;
4-{([1-(4-chlorophenyl)-9-methyl-6-oxo-6,9-dihydro-1H-purin-2-yl]oxy}-2,3-difluorobenzonitrile;
5-(9-Methyl-6-oxo-2-(3,4,5-trifluorophenoxy)-6H-purin-1(9H)-yl)picolinonitrile;
5-[2-chloro-3-(trifluoromethyl)phenoxy]-6-(4-fluorophenyl)[1,3]thiazolo[5,4-d]pyrimidin-7(6H)-one;
9-ethyl-1-(4-fluorophenyl)-2-(2,3,4-trifluorophenoxy)-1,9-dihydro-6H-purin-6-one;
9-ethyl-1-(4-fluorophenyl)-2-(2,3,5-trifluorophenoxy)-1,9-dihydro-6H-purin-6-one;
9-ethyl-1-(4-fluorophenyl)-2-(2,4,5-trifluorophenoxy)-1,9-dihydro-6H-purin-6-one; or
9-ethyl-1-(4-fluorophenyl)-2-(2,4,6-trifluorophenoxy)-1,9-dihydro-6H-purin-6-one.

* * * * *